United States Patent
Bates et al.

(10) Patent No.: US 12,165,015 B2
(45) Date of Patent: Dec. 10, 2024

(54) DATA CONVERSION/SYMPTOM SCORING

(71) Applicant: The Phoenix Partnership (Leeds) Ltd, Leeds (GB)

(72) Inventors: Chris Bates, Leeds (GB); Matthew Stickland, Leeds (GB); Frank Hester, Leeds (GB); Ankit Sharma, Leeds (GB)

(73) Assignee: THE PHOENIX PARTNERSHIP (LEEDS) LTD, Horsforth (GB)

( * ) Notice: Subject to any disclaimer, the term of this patent is extended or adjusted under 35 U.S.C. 154(b) by 1041 days.

(21) Appl. No.: 17/027,918

(22) Filed: Sep. 22, 2020

(65) Prior Publication Data
US 2021/0089965 A1    Mar. 25, 2021

(30) Foreign Application Priority Data
Sep. 23, 2019    (GB) .................................... 1913666

(51) Int. Cl.
*G06N 20/00*    (2019.01)
*G16H 10/60*    (2018.01)
*G16H 50/20*    (2018.01)

(52) U.S. Cl.
CPC ............. *G06N 20/00* (2019.01); *G16H 10/60* (2018.01); *G16H 50/20* (2018.01)

(58) Field of Classification Search
CPC ........ G06N 20/00; G06N 3/044; G06N 3/048; G06N 3/084; G06N 5/01; G06N 20/20;
(Continued)

(56) References Cited

U.S. PATENT DOCUMENTS

| | | | | |
|---|---|---|---|---|
| 2012/0290319 | A1* | 11/2012 | Saria | G16H 15/00 705/3 |
| 2018/0315507 | A1 | 11/2018 | Mortazavi et al. | |
| 2021/0064388 | A1* | 3/2021 | Gardner | G06F 11/3055 |

FOREIGN PATENT DOCUMENTS

| | | | | |
|---|---|---|---|---|
| WO | 9705553 | A1 | 2/1997 | |
| WO | WO-2014201515 | A1 * | 12/2014 | G06F 19/3431 |
| WO | 2019070200 | A1 | 4/2019 | |

OTHER PUBLICATIONS

Devlin, Hannah, Hospital develops AI to identify patients likely to skip appointments. The Guardian Apr. 12, 2019. Accessed at https://www.theguardian.com/society/2019/apr/12/hospital-develops-ai-to-identify-patients-likely-to-skip-appointments. 10 pages.
(Continued)

*Primary Examiner* — Pei Yong Weng
(74) *Attorney, Agent, or Firm* — Hamilton, Brook, Smith & Reynolds, P.C.

(57) ABSTRACT

A computer system for generating a quantitative value relating to a negative health outcome, the computer system comprising: a conversion module configured to receive multiple sets of data items associated with patients and each comprising a descriptor and the time at which that event impacted the patient. The conversion module generates a training data structure which comprises for each patient an array of selected features, each selected feature associated with a numerical value representing a score indicative of the relevance of that feature to the prediction of the negative health outcome, and a label indicating if the patient exhibits the negative health outcome; and a machine learning model which is trained using the training data structure so as to be operable to generate a quantitative value relating to a negative health outcome for a patient with at least some of the features.

20 Claims, 24 Drawing Sheets

(58) Field of Classification Search
CPC ........ G06N 3/045; G16H 10/60; G16H 50/20; G16H 50/70; G16H 50/30; G06F 18/23213; G06F 18/24323
See application file for complete search history.

(56) References Cited

OTHER PUBLICATIONS

Extended European Search Report in European Patent Application No. 20196573.8 dated Feb. 11, 2021, 12 pages.

* cited by examiner

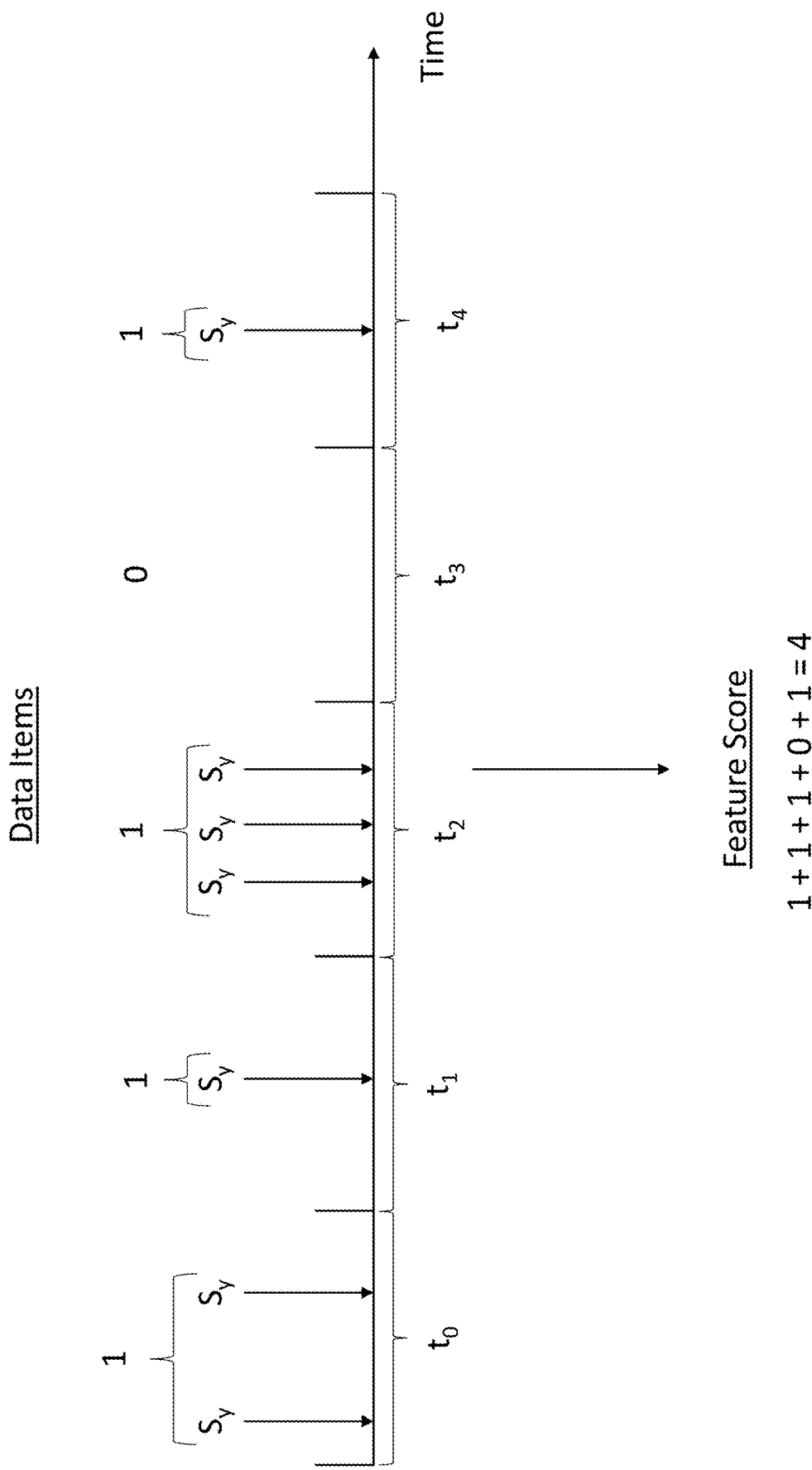

| Onset Time | Descriptor | Location recorded |

Data Item

Figure 7

Data Item: | Onset Time | Descriptor | Location recorded |

Figure 10

DATA CONVERSION/SYMPTOM SCORING

CROSS-REFERENCE TO RELATED APPLICATION(S)

This application claims priority to GB 1913666.2, which was filed on Sep. 23, 2019, and is hereby incorporated by reference in its entirety for all purposes.

TECHNICAL FIELD

The present disclosure relates to a computer system for generating a quantitative value relating to a negative health outcome. The system may be used as a diagnostic aid for use by medical practitioners or as a health management tool by consumers.

BACKGROUND

Making evaluations and predictions as to negative health outcomes for patients is an important stage in the provision of healthcare for patients. Such evaluations and predictions include the diagnosis of diseases in patients, the predicting of risks of developing diseases, and the predicting of risk of complications in patients diagnosed with a certain disease. Ovarian cancer, for example, is very difficult for healthcare staff to diagnose from patient symptoms, and often remains undetected until later stages of the cancer, when treatment is less likely to be successful. Early stage diagnosis of this disease and other disease is key to providing effective treatment.

Patient health records are now often available in databases. Such a database may store shared patient records from a plurality of different sources. Multiple records for a patient may be collected from different branches of the health service, for example, from both primary care and secondary care sources. The different records for a patient are collected together to form a single patient record for that patient that is stored in a database. This shared patient record can then be accessed by healthcare staff from different hospitals, surgeries, etc, in order to provide them with an extensive record of the patient's medical history.

SUMMARY

The increased availability of patients' electronic health care records has caused the inventors to consider the design of a computer system for using the data items contained therein to assist in diagnosing and predicting negative health outcomes for the patient.

Machine learning models, such as neural networks, may play a valuable role in diagnosing and making predictions for patients. It has been demonstrated that neural networks can be trained to make predictions of cardiovascular risk from retinal scans. Furthermore, machine learning models can be trained to spot cancerous tissue with greater accuracy than the human eye.

One proposal is to apply machine learning models to perform data analysis of patient records. Data from a GP (General Practitioner) could be fed into a machine learning model for analysis. Additionally, health record data could be combined with genomics data and provided to a machine learning model. In addition to genomics data, data from wearables, or any other data linkable to the patient in any way could be combined with health record data for analysis.

However, to achieve these desirable outcomes it has been necessary to consider the manipulation of the data structures, and the manner in which models are trained to be useable in a variety of contexts.

According to a first aspect, there is provided a computer system for generating a quantitative value relating to a negative health outcome for a patient, the computer system comprising: a conversion module configured to receive multiple sets of data items, each set associated with the patient and each data item comprising a descriptor and the time at which that event impacted the patient, the conversion module configured to generate at least one training data structure which comprises for each patient an array of selected features, each selected feature associated with a numerical value representing a score indicative of the relevance of that feature to the prediction of the negative health outcome, and a label indicating if the patient exhibits the negative health outcome; and at least one machine learning model which is trained on the at least one training data structure so as to be operable to generate a quantitative value relating to a negative health outcome for a patient with at least some of the features but for which the status of the negative health outcome is unknown.

In some embodiments, the conversion module is configured to generate multiple training data structures, each training data structure having a different label corresponding to a different respective negative health outcome; and multiple machine learning models, each model having been trained in relation to one of the respective negative health outcomes.

In some embodiments, each machine learning model which is trained with a label indicating a respective different negative health outcome is trained with a training data structure having a common set of selected features.

In some embodiments, each machine learning model which is trained relating to a different respective negative health outcome is trained using a training data structure with different sets of selected features with the different sets comprising at least some common features.

In some embodiments, the conversion model is configured to receive additional data items in a patient's set and to modify the score(s) indicating the relevance of each feature affected by the additional data items for that patient set and generate a new training data structure including the modified score or scores for that patient.

In some embodiments, the conversion module is configured to generate the score using a time related manipulation of numerical values associated with the descriptors of the data items.

In some embodiments, the time related manipulation comprises a decay model wherein the score associated with a particular selected feature is reduced with time if that feature is not represented in subsequently received data items.

In some embodiments, the conversion model is configured to receive an additional data item in a patient's set and to generate a new training data structure including a new feature described by the additional data item for that patient set, wherein the computer system comprises a further machine learning model trained using the new training data structure.

In some embodiments, the conversion module is configured to receive the multiple patients' sets of data items in a raw format and to map the data items of the raw format to a standard format comprising a pre-determined indicator code for each feature to form part of the descriptor.

In some embodiments, the features are selected from: symptoms; test or procedures carried out on the patient; test results for the patient; personal data for the patient; contextual data for the patient; and family history.

In some embodiments, the computer system comprises an interface for receiving the personal data, the personal data including sensor data derived from at least one sensor configured to determine physiological information about the patient, age of the patient, weight of the patient, genomic information of the patient, ethnicity of the patient, blood type of the patient, etc.

In some embodiments, the computer system is configured to receive the sensor data from at least one wearable device worn by the patient.

In some embodiment, the computer system is configured to derive the contextual data from an external data source, the contextual data comprising location data, physical environmental data (e.g. weather), social environmental data (e.g. deprivation index), or social data for a patient (e.g. the marital status of the patient).

In some embodiments, the negative health outcome is a disease or a disease complication. The system and methods described herein can be used in principle for any disease or disease complication. Some examples are given here but are not to be considered as limiting:

Cardiovascular diseases, including:
    Coronary artery diseases (CAD), such as angina and myocardial infarction (commonly known as a heart attack)
    Stroke
    Heart failure
    Hypertensive heart disease
    Rheumatic heart disease
    Cardiomyopathy
    Heart arrhythmia
    Congenital heart disease
    Valvular heart disease
    Carditis, aortic aneurysms
    Peripheral artery disease
    Thromboembolic disease
    Venous thrombosis.

Cancers, including:
    Anal cancer
    Bile duct cancer (cholangiocarcinoma)
    Bladder cancer
    Bowel cancer
    Brain tumours
    Breast cancer
    Cancer of unknown primary
    Carcinoid tumours
    Cervical cancer
    Connective tissue cancer
    Endocrine cancer
    Eye cancer
    Gall bladder cancer
    Head and neck cancers
    Kaposi's sarcoma
    Kidney cancer
    Leukaemia
    Liver cancer
    Lung cancer
    Lymphoma
    Melanoma
    Mesothelioma
    Multiple myeloma
    Ovarian cancer
    Pancreatic cancer
    Penis cancer
    Peritoneal cancer
    Primary bone cancer
    Prostate cancer
    Secondary Bone Cancer
    Skin cancer
    Soft tissue cancers
    Stomach and oesophageal cancer
    Testicular cancer
    Thymus cancer
    Thyroid cancer
    Uterine cancer
    Vulvar and vaginal cancers Respiratory diseases, including:
    Asthma
    Bronchiectasis
    Chronic obstructive lung disease
    Chronic obstructive pulmonary disease
    Bronchitis and emphysema
    Chronic rhinosinusitis
    Hypersensitivity pneumonitis
    Lung cancer and neoplasms of respiratory and intrathoracic organs
    Lung fibrosis
    Chronic pleural diseases
    Pneumoconiosis
    Pulmonary eosinophilia
    Pulmonary heart disease and diseases of pulmonary circulation including pulmonary embolism, pulmonary hypertension and cor pulmonale
    Rhinitis
    Sarcoidosis
    Sleep apnea syndrome
    Diabetes
    When the disease is diabetes, examples of disease complications include nephropathy, neuropathy, retinopathy, and diabetic foot (amputation). When the disease is atrial fibrillation, disease complications include stroke and thromboembolism.

In some embodiments, the conversion module comprises at least one computer on which is executed a computer program configured to generate the at least one training data structure from the received multiple sets of data items, and an interface for receiving the multiple patient sets of data items and connected to supply them to the at least one computer.

According to a second aspect, there is provided a computer implemented method for training a machine learning model so as to be operable to generate a quantitative value relating to a negative health outcome for a patient, the method comprising: generating at least one training data structure from multiple patient sets of data items, each patient set associated with a patient and each data item comprising a descriptor of a health impacting event and the time at which that event impacted the patient, wherein the training data structure comprises for each patient an array of selected features, each selected feature associated with a numerical value representing a score indicative of the relevance of that feature to the prediction of the negative health outcome, and a label indicating if the patient exhibits the negative health outcome: applying the at least one training data structure to at least one machine learning model to thereby train the machine learning model.

In some embodiments, the method comprises the step of using multiple said training data structures to train respective multiple machine learning models, each training data structure having a different label relating to a different negative health outcome.

In some embodiments, the method comprises the step of training each machine learning model which is trained with a label indicating a respective different negative health outcome with a training data structure having a common set of selected features.

In some embodiments, the method comprises the step of training each machine learning model which is trained relating to a different respective negative health outcome using a training data structure with different sets of selected features, with the different sets comprising at least some common features.

In some embodiments, the method comprises the steps of: receiving at the conversion model, additional data items in a patient's set; modifying the score(s) indicating the relevance of each feature affected by the additional data items for that patient set; and generating a new training data structure including the modified score or scores for that patient.

In some embodiments, the method comprises the step of generating the score using a time related manipulation of numerical values associated with the descriptors of the data items.

In some embodiments, the time related manipulation comprises a decay model, the method comprising reducing with time the score associated with a particular selected feature if that feature is not represented in subsequently received data items. The time related manipulation may be a decay function, in the form of a sigmoid. The "width" of the sigmoid may vary with the feature, for example to accommodate the likelihood of different historical relevance of different symptoms.

In some embodiments, the method comprises receiving an additional data item in a patient set and generating a new training data structure including a new feature described by the additional data item for that patient set, wherein the method comprises training, using the new training data structure, the further machine learning model.

In some embodiments, the method comprises receiving at the conversion module, the multiple patients' sets of data items in a raw format and mapping the data items of the raw format to a standard format comprising a pre-determined indicator code for each feature to form part of the descriptor.

In some embodiments, the method comprises selecting the features from: symptoms; test or procedures carried out on the patient; test results for the patient; personal data for the patient; contextual data for the patient; and family history.

In some embodiments, the method comprises receiving, at an interface of the computer system, the personal data, the personal data including sensor data derived from at least one sensor configured to determine physiological information about the patient, age of the patient, weight of the patient, genomic information of the patient, ethnicity of the patient, blood type of the patient, etc.

In some embodiments, the method comprising receiving the sensor data from at least one wearable device worn by the patient.

In some embodiment, the method comprising deriving the contextual data from an external data source, the contextual data comprising location data, physical environmental data (e.g. weather), social environmental data (e.g. deprivation index), or social data for a patient (e.g. the marital status of the patient).

In some embodiments, the negative health outcome is a disease or a disease complication.

In some embodiments, the negative health outcome comprises a disease in the group: cardiovascular diseases, cancers, respiratory diseases, and diabetes.

In some embodiments, the negative health outcome is a disease complication comprising at least one of diabetic complications—such as nephropathy, neuropathy, retinopathy, and diabetic foot (amputation)—or atrial fibrillation (e.g. stroke and thromboembolism).

In some embodiments, the conversion module comprises at least one computer on which is executed a computer program, the method comprising: generating, by the computer program, the at least one training data structure from the received multiple sets of data items; receiving at an interface of the conversion module, the multiple patient sets of data item; and supplying, by the interface, the multiple patient sets of data items to the at least one computer.

BRIEF DESCRIPTION OF THE DRAWINGS

FIG. 2A is a schematic illustration of a process for producing a feature score from raw data;

FIG. 7 is an example illustration of a standard format data item used to generate a training data set;

FIG. 10 is an example illustration of a standard format data item used to generate an operating data set;

DETAILED DESCRIPTION

Figure 1:
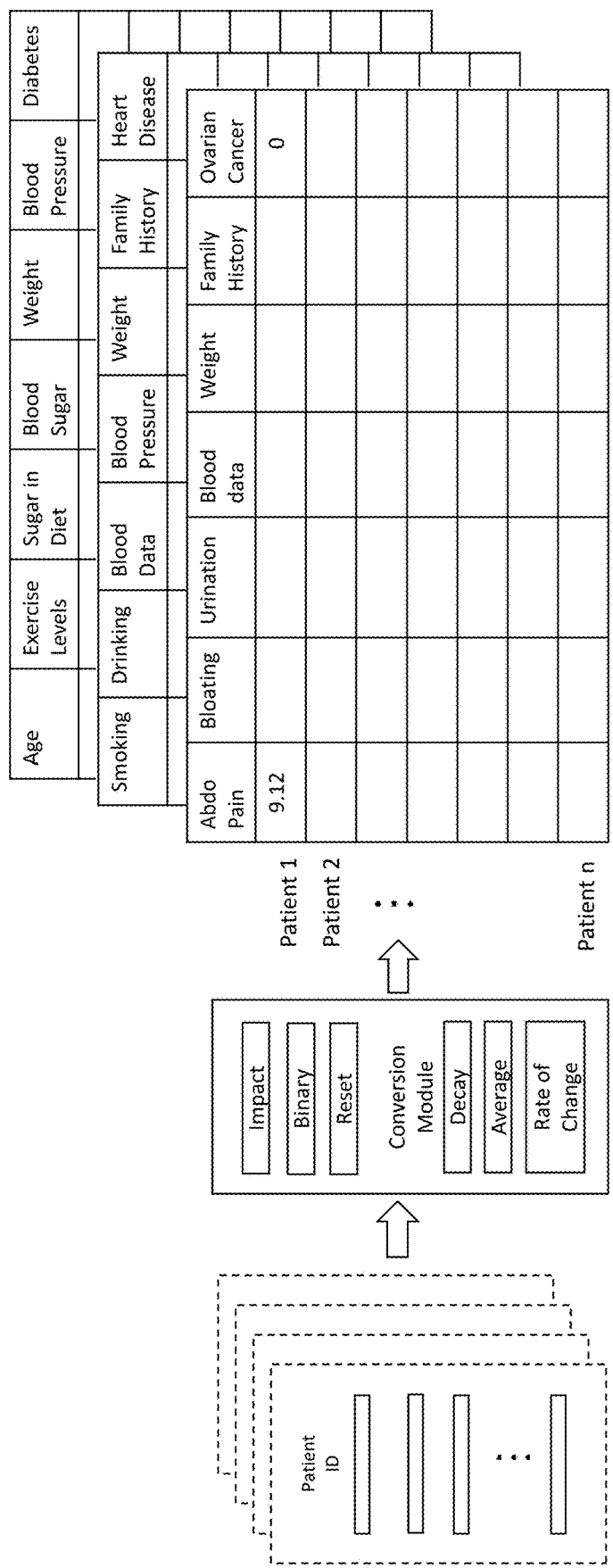
FIG. 1 is a schematic illustration of the process for producing a sets of training data from sets of data items associated with patients.

According to embodiments of the application, a system comprising a conversion module is provided. The conversion module receives a series of data items associated with a patient and provides a series of scores for the patient based on the series of data items. Each score represents a feature (e.g. a symptom) associated with a patient. At least one of these scores is associated with that patient and a label for a machine learning model. The remaining scores are used as inputs to the model for training the model. The scores for the patient are part of a training data set comprising scores associated with a number of patients that are produced by the conversion module. The training data set is used to train a machine learning model. The conversion module may produce several different training data sets, each for training a different machine learning model.

Furthermore, according to embodiments of the application, a conversion module running on a system is configured to provide from a series of data items for a patient, a series of scores based on the series of data items for use during an operating phase of a machine learning model. This series of scores for a patient is referred to herein as an operating data set. Each score represents a feature (e.g. a symptom) associated with a patient. All of the scores in the operating data set are used as inputs to a model for determine one or more outputs from the model. The outputs indicate negative health outcomes for the patient. Models may trained with labels which specifically define a disease or disease complication. The aim is to reduce or avoid negative health outcomes. The output from one of the models may provide a treatment recommendation, e.g. a recommendation for a particular surgery or medicine. The output from one of the models may provide a personalised target or recommendation, e.g. a target or recommendation regarding diet or exercise levels. Correspondingly, the labels in the training data used to train the models relate to negative health outcomes for the patient. The labels may correspond to a treatment recommendation, e.g. a recommendation for a particular surgery or medicine. The labels may correspond to a personalised target or recommendation, e.g. a target or recommendation regarding diet or exercise levels.

Reference is made herein to a conversion module for generating the data sets (operating and training data sets) for the models. In some embodiments, this conversion module may be a single conversion module, e.g. used to generate all of the data sets (both training and operating data sets). However, in other embodiments, there may be a plurality of conversion modules, used to generate different types of data sets. For example, there may be one conversion module for generating a training data set for a model, and another conversion module for generating operating data sets for the same model. There may be different conversion modules for generating different training data sets for different models. There may be different conversion modules for generating different operating data sets for different models.

FIG. 1 is a schematic diagram illustrating how data items are used to generate training data for an artificial intelligence model. As will be explained in more detail in this description, these data items are derived from raw data records and stored in a standard format prior to being used by the conversion module to generate the training data.

There is a set of data items for each person. Each set of data items for a particular person is associated with an identifier, such as the patient identifier. These identifiers are stripped off when the training data structure is produced, such that the training data is anonymised. The sets may be in the form of lists or any other kind of array. An example of the standard format used for the data items is shown in FIG. 7. Each data item has a descriptor, which describes a feature or indicator (as will be described with reference to FIG. 7), such as a symptom, test result, treatment, or comprises contextual data (e.g. climate data). Each data item comprises an onset time. The onset time could be a date and time of day, or could just be a date. The onset time is taken to be the time at which the feature or indicator applied to the patient. For example, in the context of a symptom, the onset time is taken to be the time at which the patient experienced the symptom. In the case of climate data, the onset time is taken to be the time at which the climate data applied.

In some cases, the onset time may be the time at which the raw data record of the feature or indicator was recorded. In other cases, the onset time may be a separate time to the time at which the raw data record was recorded. In this case, the onset time is recorded in the raw data record separately to a time indicating when the raw data record itself was recorded. This 'additional' onset time in the raw data record may be recorded manually by health care staff when the raw data record is recorded. For example, a raw data item comprising an indication that a patient experienced abdominal pain on the 9 Apr. 2018 may be recorded on 18 Apr. 2018. In this example, the onset time is the 9 Apr. 2018. In another example, the raw data may be recorded on 18 Apr. 2018, with no separate indication of an onset time. In this case, the onset time in the standard format data item is 18 Apr. 2018. The granularity of the onset time may vary with the indicators and/or models.

Each data item may comprise a record of the location at which the feature or indicator was recorded, e.g. a hospital, or GP surgery, or a record that the feature or indicator was personally input by the patient.

The set of data items for any particular person may comprise a very large number of data items, spanning many decades. Sets of data items are established for a number of people or patients. The number of patients may comprise many thousands or tens of thousands of patients. Data items may be continually added to the sets of data items as new features or indicators associated with the patient are recorded.

A conversion module receives these set of data items and generates from them, multiple training data structures (or 'data sets'), each data structure comprising training data for training a different model. The conversion module removes the patient ID, such that the training data is anonymised. Each training data structure (illustrated in FIG. 1 as a table) is organised in an array of columns and rows, each row being associated with a particular person or patient, and each column being associated with a particular indicator or feature. It would be appreciated that any other organisation of the data structure may be utilised, but what is important is that scores for each patient may intersect with each particular feature or indicator. The conversion module generates a score for each intersection. For example, in the intersection box of patient 1 with abdominal pain, a score of 9.12 has been generated by the conversion module and is inserted into the training data array. Each intersection of patient and feature is assigned a particular score in a manner explained further herein. One column of the training data structure is reserved for a label for the model. In one example of a training data structure illustrated in FIG. 1, the label for a model is ovarian cancer. In this training data structure, the label column is populated with binary information (1 or 0) indicating whether or not that patient has ovarian cancer or does not have ovarian cancer. Since in the intersection between Patient 1 and Ovarian Cancer the score is zero, Patient 1 in the example does not have ovarian cancer.

Models may be generated for predicting or evaluating a variety of different negative health outcomes, each model using a different training data structure. The negative health outcomes include contraction of a disease or disease complication. As shown in FIG. 1, other training data structures are generated from sets of data items for patients. The example training data structures include a training data structure for training a model for predicting heart disease in a patient. In this case, the label column is populated with binary information (1 or 0) indicating whether or not that patient developed heart disease. Suitable features or indicators (having predictive value for heart disease, e.g. smoking) are used to generate scores for the training data structure for this model. Also shown in FIG. 1 is a training data structure for training a model for predicting diabetes in a patient. In this case, the label column is populated with binary information (1 or 0) indicating whether or not that patient developed diabetes. Suitable features or indicators (having predictive value for diabetes, e.g. age or exercise levels) are used to generate scores for the training data structure for this model.

In the example training data structures shown in FIG. 1, different features for which scores are provided are included. For example, in the training data structure for the ovarian cancer model, scores for Abdominal Pain are provided. Such scores are not provided in the training data structure for the Heart Disease model, but scores for blood pressure are instead provided. However, in other example embodiments of this application, the set of features that are scored in the different training data structures may be the same, with only the selected labels being different between the training data sets.

Even in cases where the same feature is scored and inserted into a training data set, the score for that feature for a patient may vary between different training data sets for training different models. In other words, a different set of transformations may be applied to determine a score for the same features for training data sets associated with different models. For example, in FIG. 1, the feature "weight" is included in the training data sets for each of diabetes, heart disease, and ovarian cancer. However, the score associated with weight for Patient 1, may vary between data sets. This reflects the fact that the conversion module applies different rules/transformations when determining the score depending upon the model for which the training data set is produced. Even though, in the set of data items for patient 1, the descriptors indicating Patient 1's weight are the same when the conversion module generates the training data sets for different models, the conversion module outputs different scores associated with the 'weight' feature in the training data sets for different models by applying different transformations to the set of data items for patient 1.

When establishing a training data set for a particular model, the features or indicators to be used as columns in the data sets may be determined manually or automatically.

Models may be established for particular diseases, such as ovarian cancer or diabetes, and/or for particular disease outcomes. A disease outcome might, for example, be a complication which is expected to arise at least some of the time with a particular disease. For example, foot ulcers, amputation and blindness are common complications of diabetes. However, not all patients suffer from these complications, and one value of these machine learning models is to establish the features or indicators which may be more heavily associated with complications and, conversely, with good outcomes even for people having a particular disease.

It will be appreciated that models for disease outcomes are trained on people who are known to have the particular disease. That is, the training data set would include only patients or people with that disease. The conversion module would search the sets of data items associated with people to pick out sets of data items associated with people who had a record of having that particular disease and then construct a training data set based on the sets of data items associated with such people. The label column in each case represents the disease or disease outcome.

In addition to health related data of the type that may be included in a patient's health record, the training data set may accommodate different kinds of additional data. The only criteria is that the additional data needs to be associated with the person. Additional data may be associated with a time of occurrence (e.g. climate data) or may be a permanent feature associated with a patient, such as genomic data or blood data. Additional data may be environmental data. Such environmental data be derived from resources which provide environmental data pertaining to a particular location. This could be recorded based upon the normal location of a patient (for example their home address), or by tracking their location based on a device such as a mobile phone that they may be carrying with them. Such mobile devices may have an application embedded in the phone which enables environmental data to be assessed and recorded in association with time. Such environmental data could include barometric pressure, pollution levels, average temperatures, average humidity levels etc.

Another kind of additional data is social data or deprivation indicators. These are based generally on a permanent location of a person, such as their normal home address. There may be other social indicators associated with a particular person which may also feed into a deprivation score.

Other additional data may include diet. This could be recorded as the type of food consumed, calorie count etc. This could be recorded as a result of history being taken in a doctor's surgery or other medical establishment, or be self-reported. Such data could also include drinking levels or smoking levels.

Another form of additional data is data which may be derived from wearables, such as sensor data which could sense physiological measurements from a user. These may include blood pressure, heart rate, skin temperature, blood glucose etc. Such wearables can provide a continuous time related data stream of such sensed data. In order to establish standard format data items for the set of data items to be associated with a particular patient, a granularity is determined for extracting and converting the stream of data into those data items. For example, a measurement might be recorded each day, week or month.

Another form of additional data, which is also personal data, could relate to a person's general state of health, such as their activity levels.

It will readily be appreciated that this is not an exhaustive list of data that could be used to generate training data sets. It is important to recognise, however, that data in addition to symptom data, or medical data, the additional data may usefully be utilised to train models relating to diseases or disease complications. In fact, it is possible to train a model for a particular disease or a disease complication using solely data which is not necessarily health or symptom related. That is, a model could be trained using only contextual data for a patient (such as environmental data etc.). What is important is that each model can indicate a requirement for input data when the model is to be executed on a particular input data set to generate a particular requested output.

Figure 1A:
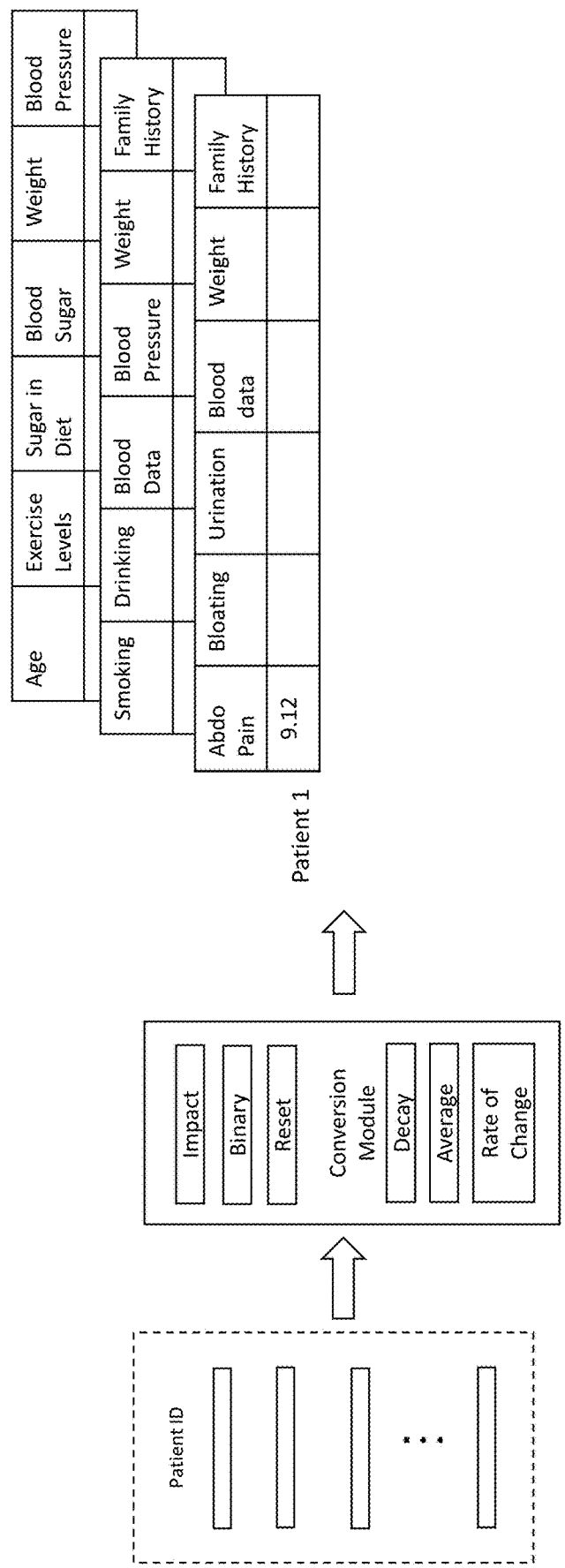
FIG. 1A is a schematic illustration of the process for producing a sets of operating data from a set of data items associated with a patient.

FIG. 1A is a schematic diagram illustrating how data items which have been converted into a standard format are used to generate data (referred to herein as 'operating data') for input to a trained artificial intelligence model during an operating phase to obtain one or more results. When the model is operated to determine an outcome for a patient, data from a single patient is applied to the model and an outcome value is derived.

A set of data items is associated with a particular person, who is identified by an identifier, such as a patient identifier. This set may be in the form of lists or any other kind of array. An example of a data item is shown in FIG. 10. Each data item has a descriptor which describes a feature or indicator (as already described with reference to FIG. 7), such as a symptom test result, treatment or comprises contextual data (e.g. climate data). Each data item comprises an onset time. The onset time could be a date and time of day, or could just be a date. The onset time is taken to be the time at which the feature or indicator applied. For example, in the context of a symptom, the onset time is taken to be the time at which the patient experienced the symptom. In the case of climate data, the onset time is taken to be the time at which the climate data applied.

In some cases, the onset time may be the time at which the raw data record of the feature or indicator was recorded. In other cases, the onset time may be a separate time to the time at which the raw data record was recorded. In this case, the onset time is recorded in the raw data record separately to a time indicating when the raw data record itself was recorded. This 'additional' onset time in the raw data record may be recorded manually by health care staff when the raw data record is recorded. For example, a raw data item comprising an indication that a patient experienced abdominal pain on the 9 Apr. 2018 may be recorded on 18 Apr. 2018. In this example, the onset time is the 9 Apr. 2018. In another example, the raw data may be recorded on 18 Apr. 2018, with no separate indication of an onset time. In this case, the onset time in the standard format data item is 18 Apr. 2018.

The granularity of the onset time may vary with the indicators and/or models. Each data item comprises a record of the location at which the feature or indicator was recorded, e.g. a hospital, GP surgery, or a record that the feature or indicator was personally input by the patient.

The set of data items for any particular person may comprise a very large number of data items, spanning many decades.

A conversion module receives the set of data items for a patient and generates from them, a set of operating data for input to one or more models. The conversion module produces many different sets of operating data for different patients. The sets of operating data are determined one at a time, with each set of operating data being applied separately to an appropriate model to determine an outcome. Since the one or more models obtain results separately for different patients, a single set of operating data is produced for each patient that a model is run for. As shown in FIG. 1A, a set of operating data comprises a single row of scores (each score being associated with a particular indication or feature) associated with a particular person or patient. It would be appreciated that any other organisation of the data structure may be utilised, but what is important is that the operating data set for a patient comprises a set of scores associated with that patient. The conversion module generates a score for each feature or indicator. In the example of FIG. 1A, a score of 3.6 is assigned for abdominal pain for patient 1. This score has been generated by the conversion module and is inserted into the operating data set.

Unlike the training data set, an operating data set does not include labels for the models. As shown in the example of FIG. 1A, the first example of an operating data set that is shown does not include the indication of ovarian cancer present in the example training data set illustrated in FIG. 1. In the operating phase, the output from the model is used to determine the probability of a patient having ovarian cancer. An output of 1 from the model may indicate that the patient has ovarian cancer, whilst an output of 0 from the model may indicate that the patient does not have ovarian cancer. Numbers between 0 and 1 provide an indication of the probability that a patient has ovarian cancer. Ovarian cancer is one example, but different models may be applied to generate outputs for a variety of different negative health outcomes. Therefore, an operating data set for input to a particular model contains scores for the same features or indicators in the training data set used to train the model, without the labels that are included in the training data set.

The output value may be the contribution of two classification outputs—(i) the probability that the person will contract ovarian cancer; (ii) the probability that the person will not contract ovarian cancer.

As shown in FIG. 1A, other operating data structures are generated from sets of data items for patients. The example operating data structures include an operating data structure for input to a model for predicting heart disease in a patient. Suitable features or indicators (having predictive value for diabetes, e.g. smoking) are used to generate scores for the operating data structure for this model. These features match the features used in the corresponding training data structure shown in FIG. 1. Also shown in FIG. 1A, is an operating data structure for input to a model for predicting diabetes in a patient. Suitable features or indicators (having predictive value for heart disease, e.g. age or exercise levels) are used to generate scores for the training data structure for this model. These features match the features used in the corresponding training data structure shown in FIG. 1.

In the example operating data structures shown in FIG. 1A, different features for which scores are provided are included. For example, in the operating data structure for the ovarian cancer model, scores for Abdominal Pain are provided. Such scores are not provided in the operating data structure for the Heart Disease model, but scores for blood pressure are instead provided. However, in other example embodiments of this application, the set of features that are scored in the different operating data structures may be the same.

Even in cases where the same feature is scored and inserted into an operating data set, the score for that feature for a patient may vary between different operating data sets for operating different models. In other words, a different set of transformations may be applied to determine a score for the same features for operating data sets associated with different models. For example, in FIG. 1A, the feature "weight" is included in the operating data sets for each of diabetes, heart disease, and ovarian cancer. However, the score associated with weight for Patient 1, may vary between data sets. This reflects the fact that the conversion module applies different rules/transformations when determining the score depending upon the model for which the operating data set is produced. Even though, in the set of data items for patient 1, the descriptors indicating Patient 1's weight are the same when the conversion module generates the operating data sets for different models, the conversion module outputs different scores associated with the 'weight' feature in the operating data sets for different models by applying different transformations to the set of data items for patient 1.

When establishing an operating data set for a particular model, the features or indicators to be scored in that operating data set may be determined manually or automatically.

In addition to health related data of the type that may be included in a patient's health record, the operating data set may accommodate different kinds of additional data. The only criteria is that the additional data needs to be associated with the person. Additional data may be associated with a time of occurrence (e.g. climate data) or may be a permanent feature associated with a patient, such as genomic data or blood data. Additional data may be environmental data. Such environmental data be derived from resources which provide environmental data pertaining to a particular location. This could be recorded based upon the normal location of a patient (for example their home address), or by tracking their location based on a device such as a mobile phone that they may be carrying with them. Such mobile devices may have an application embedded in the phone enables environmental data to be assessed and recorded in association with time. Such environmental data could include barometric pressure, pollution levels, average temperatures, average humidity levels etc. The additional data may be social environmental data, such as, deprivation score.

Another kind of additional data is social data or depravation indicators. These are based generally on a permanent location of a person, such as their normal home address. There may be other social indicators associated with a particular person which may also feed into a depravation score.

Other additional data incudes diet. This could be recorded as the type of food consumed, calorie count etc. This could be recorded as a result of history being taken in a doctor's surgery or other medical establishment, or be self-reported. Such data could also include drinking levels or smoking levels.

Another form of additional data is data which may be derived from wearables, such as sensor data which could sense physiological measurements from a user. These may include blood pressure, heart rate, skin temperature, blood glucose etc. Such wearables can provide a continuous time related data stream of such sensed data. In order to establish standard format data items for the set of data items to be associated with a particular patient, a granularity would be determined for extracting and converting the stream of data into those data items. For example, a measurement might be recorded each day, week or month.

Another form of additional data, which is also personal data, could relate to a person's general state of health, such as their activity levels.

In will readily be appreciated that this is not an exhaustive list of data that could be used to generate operating data sets. It is important to recognise, however, that data in addition to symptom data, or medical data, the additional data may usefully be utilised to provide input data to the models relating to diseases or disease complications. In fact, it is possible to generate operating data models for a particular disease or a disease complication solely using data which is not necessarily health or symptom related. That is, a model could be provided only with contextual data for a patient (such as environmental data etc.). What is important is that each model understands the feature set that has been used to train it.

The conversion module illustrated in FIGS. 1 and 1A receives data items in a standard format from which it performs feature extraction (i.e. determines the scores for input/training of machine learning models). This data in the standard format is first converted from raw data, which is obtained from patient records and, in some cases, from other sources, e.g. weather data, data input by a patient. The data items shown in FIGS. 1 and 1A are data items in the standard format. The standard format may be the format illustrated in FIGS. 7 and 10.

Figure 2:
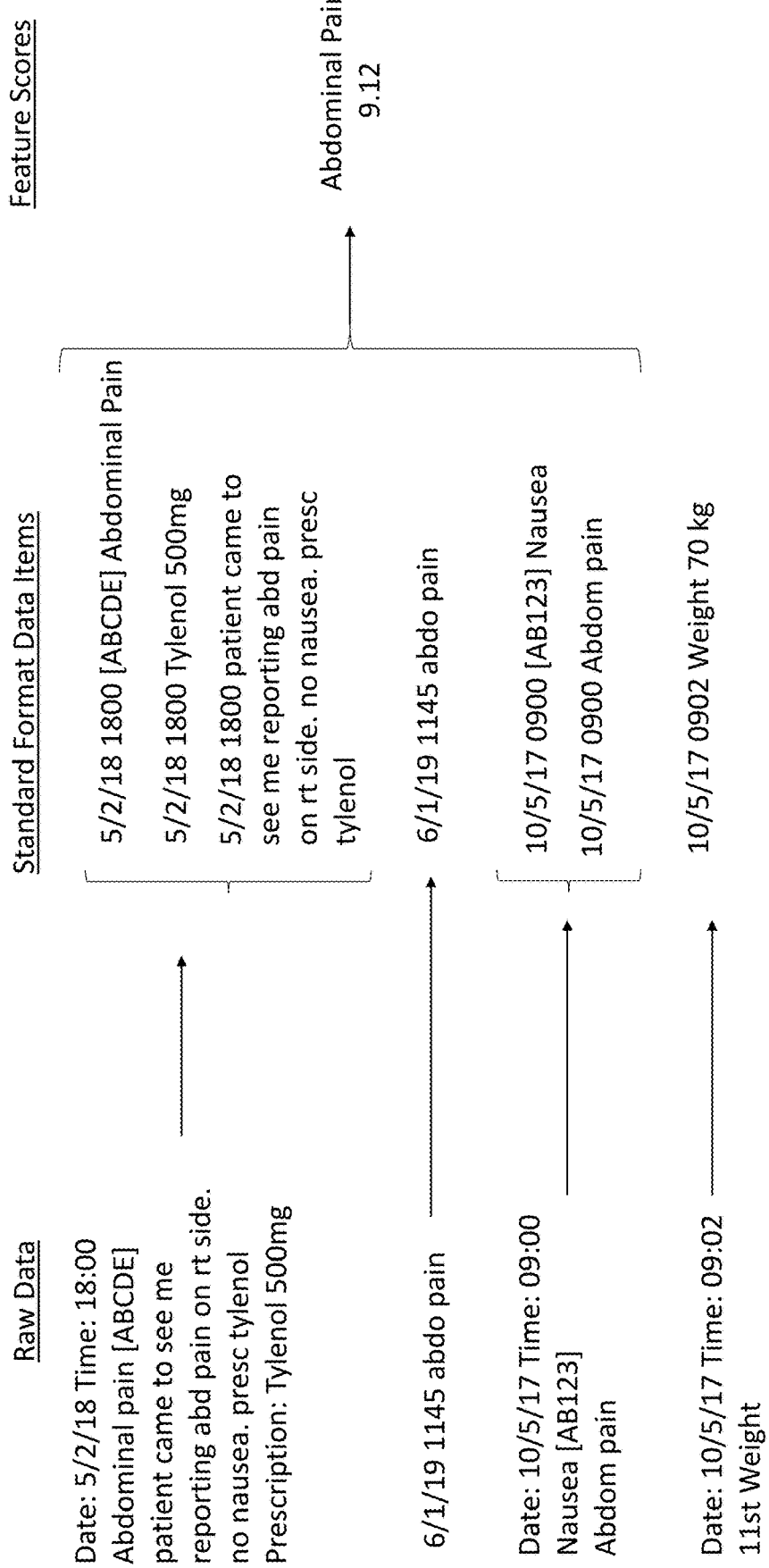
FIG. 2 is a schematic illustration of a process for producing a feature score from raw data.

Reference is made to FIG. 2, which illustrates an example of how raw data may be converted to a standard format from which feature extraction can be performed. A set of raw data items is shown in this example. This raw data represents information about a patient that may be extracted from one or more health records of a patient, or obtained from an app in the client device for example. The information may also include any other information that can be linked to the patient by any reliable means—for example the pollution, pollen, or temperature levels linked by the patient's location at that point in time. As with the indicators from the patient health records, this contextual/additional information may stored in the descriptors in the standard format data items.

The raw data information in the health records includes information regarding patient diagnoses, symptoms, treatments, test results, prescriptions, etc. The health records may be records made by a medical professional or by the patient themselves or their non-professional interested parties e.g. family. The raw data may exist in several different formats. The raw data may include encoded data (e.g. a 5 byte code or 80 bit integer) used to encode patient health records across the health service. The raw data may include, or may be wholly, free text. The raw data may include a numeric value for a measurement described by the coded or free text label. Each item of raw data then comprises at least a coded or non-coded descriptive label. Each item of raw data includes a timestamp indicating its time of recordal. At least some items of raw data may separately indicate an onset time indicating when the descriptor applied. The collection of items of raw data is associated with a person, potentially a patient, either by a unique coded identifier or by a collection of demographic values which can include date of birth, given name(s), family name(s), and gender.

A pre-processing stage (which is shown as S310 in FIG. 19, which is discussed in more detail below) is performed by the system, and involves producing a set of data items in the standard format from the raw data. The standard format may include descriptors of features comprising a coded format (e.g. the standard 5 byte code) and/or comprising free text. The raw data may include data items in the standard format, and so, for these data items, no conversion to the standard format takes place. For example, as shown in FIG. 2, the raw data includes information recording that abdominal pain was reported on 6 Jan. 2019. This information may be stored in the patient record as a data item in the standard format. When the whole data set is placed in the standard format, a copy of this data item is stored as part of the standard format data, without being converted to a different format.

Some of the raw data may not be in the standard format, but can be mapped to one or more data items in the standard format. This record in the raw data may be used to produce a plurality of data items in the standard format. As shown in FIG. 2, the raw data from a patient's record contains encoded information recording that the patient had abdominal pain on the 5 Feb. 2018. The same record on 5 Feb. 2018 also contains an encoded data item indicating that Tylenol was prescribed. The same record on 5 Feb. 2018 also contains free text describing the patient symptom of pain in the right side and indicating Tylenol was prescribed. From this raw data, three different data items in the standard format are produced by the system. Each of these standard format data items is used by the conversion module to determine the score for the feature 'abdominal pain'.

The raw data shown in FIG. 2 further includes a record of "abdo pain" made on 6 Jan. 2019 and a record of "Abdom pain" made on 10 May 2019. These records are both placed into the set of data items in the standard format with a date and time at which the indicated feature was applicable and the relevant coded or free text information. The record of the weight made on $10^{th}$ May has also been converted during pre-processing to be in the standard format from the raw format.

Once a set of data items from a patient's records has been extracted and converted to a set of items in the standard format, feature extraction (S315a or S315b in FIG. 19) is then performed by the conversion module to produce scores to be input to a machine learning model (e.g. a neural network or decision tree). In the example shown in FIG. 2, all of the data items in the standard format, with the exception of weight which is not relevant to the feature abdominal pain, are used to determine the score associated with the feature 'Abdominal Pain'. The score provides an indication of the impact of the feature and may, but not exclusively, represent the severity of the symptom. The score is provided to the machine learning model as an input when evaluating a result (e.g. patient outcome, diagnosis) for a patient.

The score that is assigned to a particular feature may be determined in dependence upon the number of times that relevant symptoms are reported and/or relevant prescriptions made. For example, in the example of FIG. 2, the score assigned for abdominal pain may be higher due to multiple data items indicating abdominal pain that are present in the standard format data.

Although the score for certain features is dependent upon the number of times that certain data items appear in the set of data items, there may be certain limitations upon the counting of data items when determining the score. Specifically, the score that is calculated in dependence upon the number of data items depends upon whether a plurality of the data items were recorded within a certain time window. If a plurality of data items were recorded within a predefined time window, those plurality of data items are counted as being a single data item for the purposes of determining the feature score. The time windows repeat sequentially one after the other.

In an example, a time period of one day may be defined for calculating a score associated with abdominal pain. A plurality of sequential time windows of one day are defined. Any data items indicating abdominal pain that fall within a particular one day time window are treated as a single data item for the purposes of determining the feature score.

Reference is made to FIG. 2A, which illustrates the use of time windows for limiting the calculation of the score in dependence upon a plurality of data items. As shown, a series of symptom data items are shown recorded with different onset times. Along the time line are shown a series of time windows, $t_0$, $t_1$, $t_2$, $t_3$, and $t_4$. The effective number of data items applied to determine the feature score is shown above each time window. For example, two data items representing symptom, $S_y$, are shown having onset times within the first time window, $t_0$. Since there is at least one data item within the time window, $t_0$, the two data items are treated as only one data item for the purposes of determining the score associated with the symptom. One data item representing symptom, $S_y$, is shown having an onset time within the second time window, $t_1$. Since there is at least one data item within the time window, $t_1$, the one data item is treated as only a single data item for the purposes of determining the score associated with the symptom. Three data items representing symptom, $S_y$, are shown having onset times within the third time window, $t_2$. Since there is at least one data item within the third time window, $t_2$, the three data items are treated as only one data item for the purposes of determining the score associated with the symptom. Within the fourth time window, $t_3$, there are no data items associated with the symptom, $S_y$. Therefore, the effective number of data items for determining the score associated with symptom, $S_y$, is zero. Within the fifth time window, $t_4$, there is only one symptom, $S_y$. Since there is at least one data item within the time window, $t_4$, there is one effective data item for the purposes of determining the score associated with the symptom.

In the example shown in FIG. 2A, the feature score is shown as being calculated by adding up the number of effective data items in each time window. However, in practice, more complex transformations mapping the data items to a feature score may be applied.

Different features may use different durations for the time windows for determining the number of effective data items for calculating a score. For example, if the data items represent abdominal pain, the time windows may each be 1 day in duration. If the data items represent weight, the time windows may each be 1 week in duration. If the data items represent blood pressure, the time windows may each be half an hour in duration.

Another way in which the score that is assigned to a particular feature may depend upon the onset time associated with the data items is through the use of a decay function. For example, when determining a score, more weight may be given to records that were made more recently or for which the onset time is more recent. For example, when determining the score to be assigned for abdominal pain, the information that abdominal pain was recorded on 5 Feb. 2018, may be given more weight than the information that abdominal pain was recorded on 10 May 2017. This 'decay function' is explained in more detail later. The calculation of the score is performed using rule based operations executed by the conversion module. The rules may be based on mathematical functions, for example linear or sigmoid. Parameters for the rules can be adjusted (gradient, minimum/maximums, coefficients) during the optimisation phase (S340 in FIG. 19) to generate the appropriate final scores. For example, abdominal pain may be adjusted to approach zero as the time elapsed since the pain approaches 2 years. The parameters and rules for determining a score for the same feature from one or more data items can differ in dependence upon the type of model. Further information regarding the different data input transformations that the conversion module is configured to perform are given below.

Although in FIG. 2 only one feature score (i.e. a score for abdominal pain) is determined from the data items stored in the standard format, in some examples, multiple feature scores could be extracted from such a set of data. For example, in addition to extracting the feature abdominal pain from the data set, a feature indicating that pain killers have been prescribed to the patient could be extracted. Each feature is represented as a score to be used as an input value to the machine learning model. The input values may be used during a training phase to train a model or during an operating phase to obtain a result.

Figure 3:
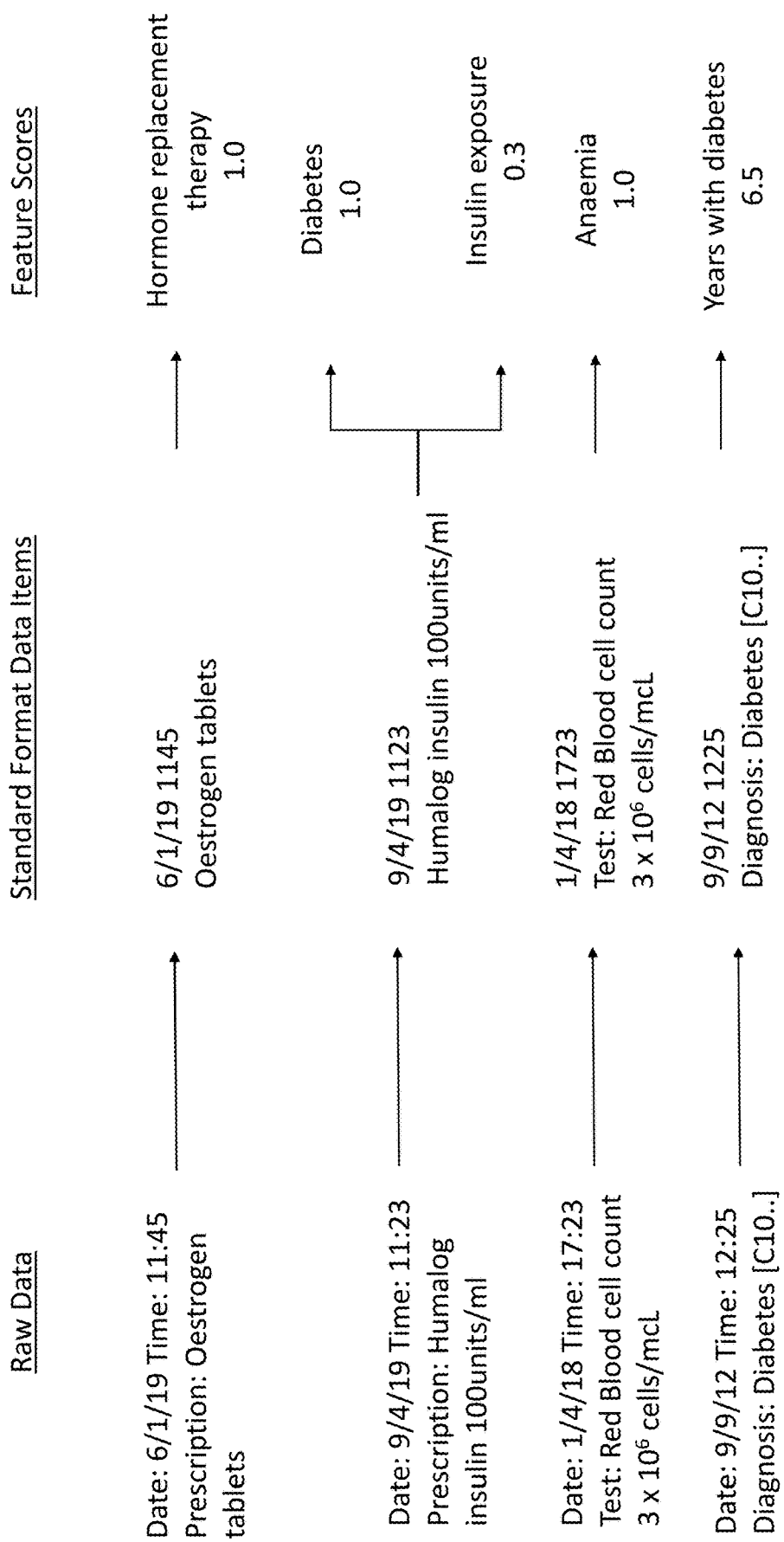
FIG. 3 is a schematic illustration of a process for producing feature scores from raw data.

When producing the scores, information in the raw data (and in the standard format data produced therefrom) may be used to indicate conditions which are not explicitly expressed in the raw data. In FIG. 3, this can be seen in the example, where the information recording that Oestrogen was prescribed is used to produce a score representing hormone replacement therapy. Even though the data item recording that Oestrogen was prescribed does not map precisely to hormone replacement therapy, this data item is mapped to a feature item representing the type of treatment (i.e. hormone replacement therapy). Similarly, as also shown in FIG. 3, a data item comprising a test result that the red blood cell count has a certain value is used by the conversion module to determine a score for Anaemia.

In some examples, the feature score extraction may involve drawing inferences about patient conditions from the data items without these conditions being explicitly recorded in the data items themselves. Different items of data encoding for, for example symptoms, test results, treatments performed, prescriptions, may be used to infer patient conditions. The feature score extraction determines patient conditions in dependence upon these items which do not directly encode for the conditions. An example of this may be seen in FIG. 2, in which a score for abdominal pain is inferred from a data item indicating nausea. In some examples, a single data item may be used by the conversion module to generate two different feature scores. For example, FIG. 3 shows a raw data item comprising a descriptor indicating that the patient was prescribed Humalog insulin. This raw data item is converted to a standard format data item also indicating that the patient was prescribed Humalog insulin. The conversion module takes this data item as an input and produces a feature score for diabetes in dependence upon the indication that the patient was prescribed Humalog insulin. Additionally, the conversion module also outputs a feature score for insulin exposure in dependence upon the indication that the patient was prescribed Humalog insulin. Hence, multiple feature scores are produced from a single data item.

Figure 4:
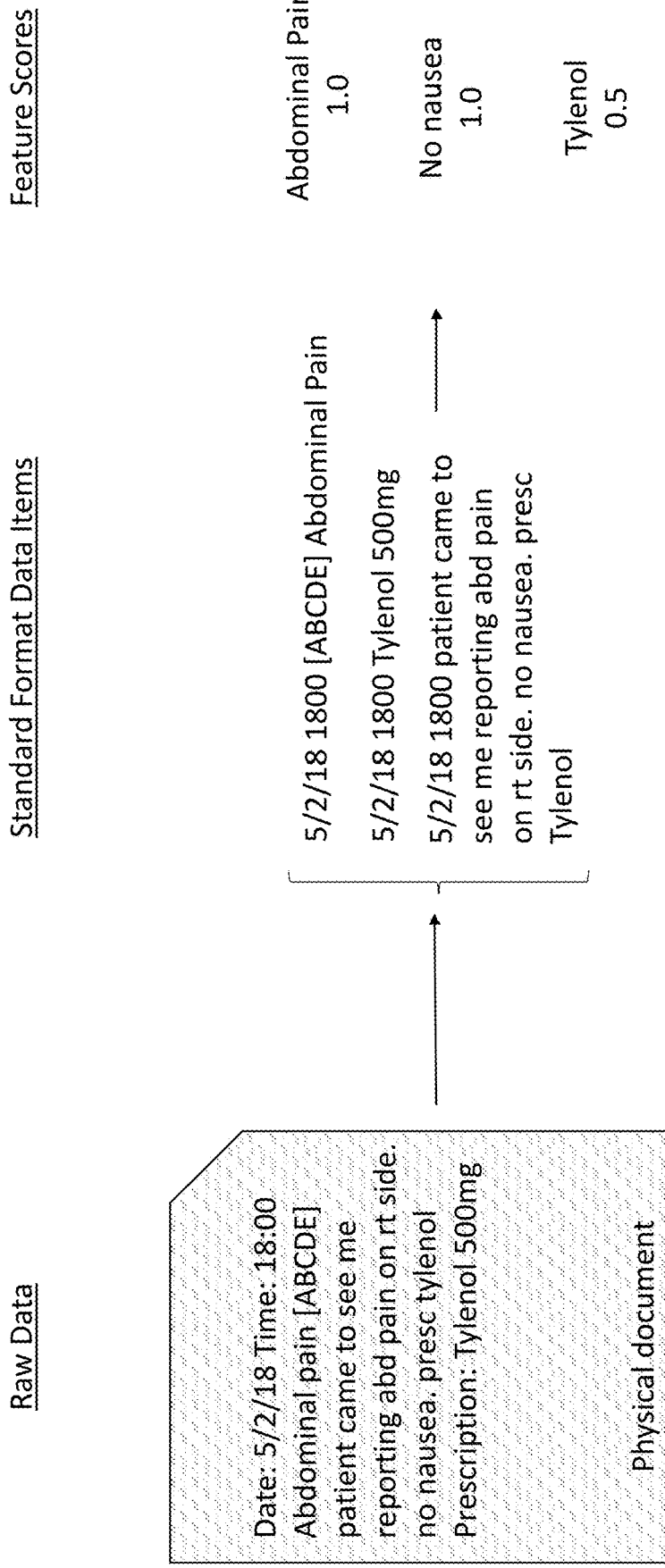
FIG. 4 is a schematic illustration of a process for producing feature scores from raw data.

In some examples, a piece of raw data may be used to determine a plurality of different scores, each associated a different feature. Reference is made to FIG. 4, which illustrates an example of this. A physical document is provided in the raw data. This document contains information recording a patient prescription and patient symptoms. From this document, a set of data items are extracted. A first data item comprises an indication of abdominal pain. A second data item comprises an indication that Tylenol was prescribed. A third data item comprises an indication of abdominal pain, no nausea, and a prescription of Tylenol. The conversion module receives the set of data items and generates a set of relevant scores in dependence upon these data items. Hence, a set of scores is generated from a single document in the raw data.

A plurality of features scores may be dependent upon a single data item. As shown in FIG. 4, at least one of the data items (with descriptor: "patient came to see me reporting abd pain on rt side. no nausea. presc Tylenol") is used by the conversion module to generate multiple feature scores, i.e. feature scores for abdominal pain, no nausea, and Tylenol. These features scores are all dependent upon a single data item in the standard format.

Figure 5:
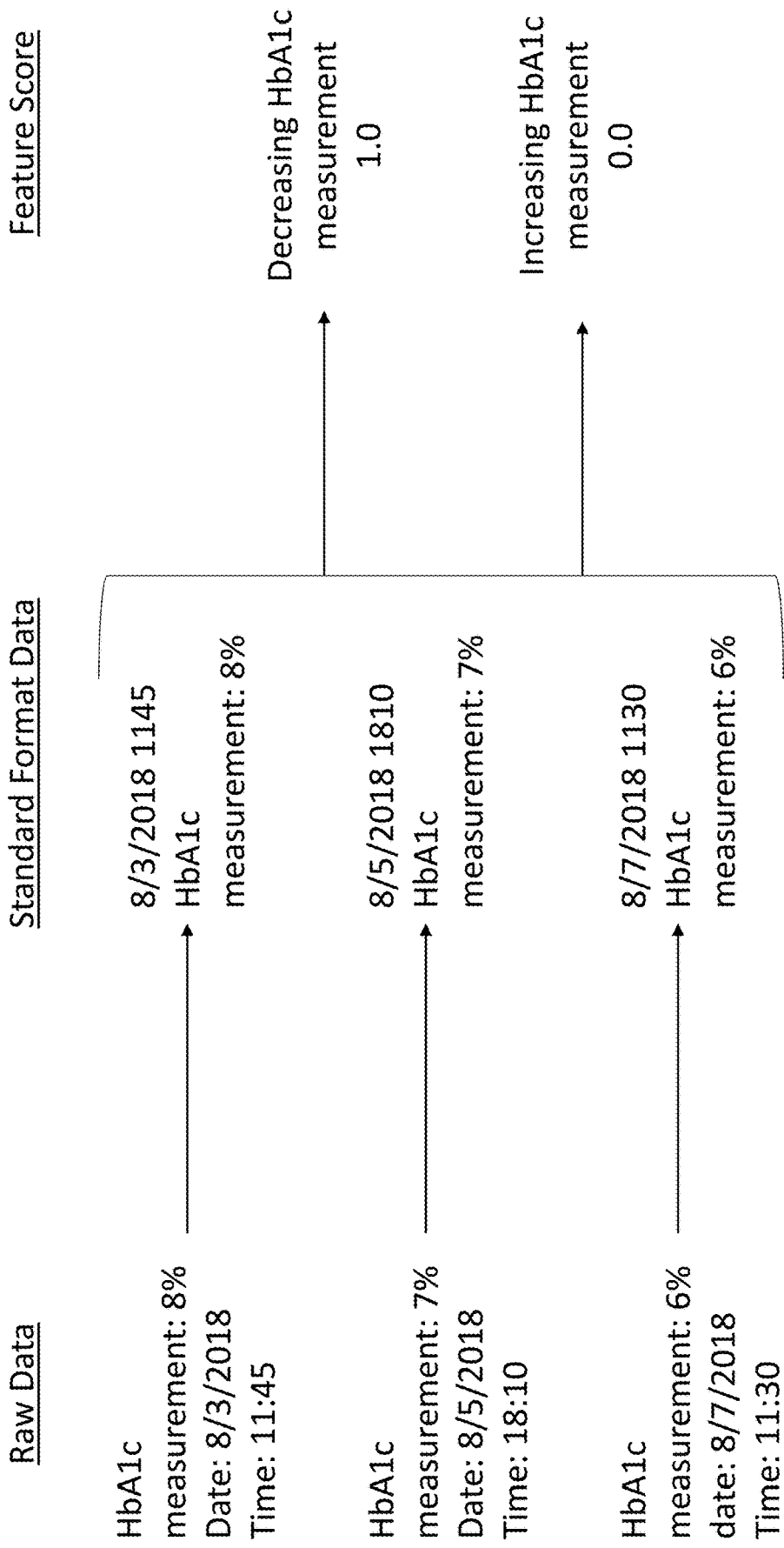
FIG. 5 is a schematic illustration of a process for producing feature scores from raw data.

Reference is made to FIG. 5, which illustrates how the conversion module determines a score in dependence upon a plurality of measurement values for a patient. The raw data includes a series of data items, each indicating a HbA1c measurement value that was recorded at a particular time. Each raw data item is converted to a standard format data item. The conversion module then determines scores that represent whether or not the HbA1c measurement value is increasing or decreasing. In the example, the conversion module outputs a score of 1.0 for the feature 'Decreasing HbA1c measurement' in dependence upon the data items, which collectively indicate HbA1c measurement values decreasing over time. The conversion module also outputs a score 0.0 for the feature 'Increasing HbA1c measurement' in dependence upon the same data items. These scores are appropriate input values for processing by a machine learning model.

Figure 5A:
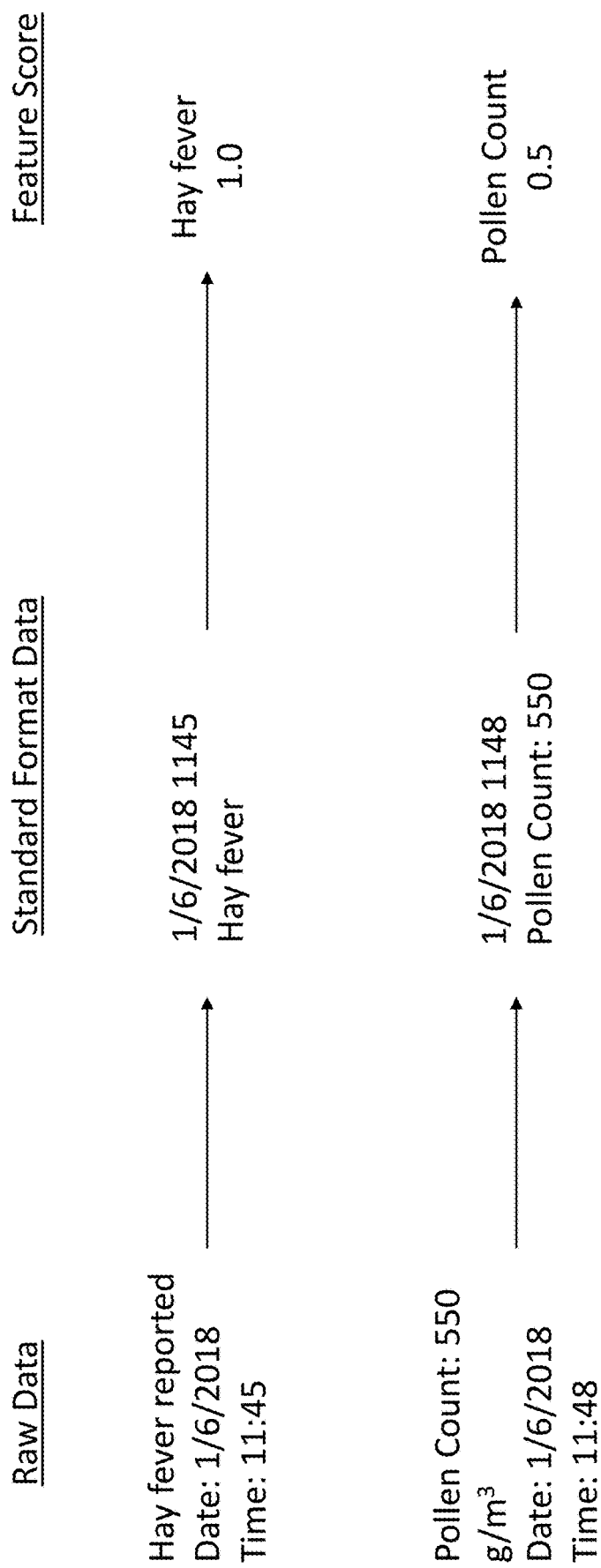
FIG. 5A is a schematic illustration of a process for producing feature scores from raw data including contextual data.

Reference is made to FIG. 5A, which illustrates an example of how contextual data in the raw data may be used to generate scores. In this example, the contextual data is environmental data (i.e. pollen count). In FIG. 5A, a first piece of raw data indicates that a patient has reported hay fever. A second piece of raw data indicates the pollen count at the approximate onset time of the hay fever record. The system produces a data item in the standard format from each of these pieces of data in the raw data. A first data item comprises a descriptor indicating that the patient has reported hay fever. A second data item comprises a descriptor indicating the pollen count. The onset time for the hay fever and the time at which the pollen count applied are substantially the same. The conversion module produces from this data item, two feature scores. A first features score is provided for hay fever. A second feature score is provided for pollen count.

As shown in FIGS. 1 and 1A, family history of a negative health outcome can be one of the features that is scored by the conversion module and used as an input value to a machine learning model.

Family history may be explicit or inferred. An explicit family history is one which is recorded in a session with a doctor or other medical staff member who ask questions of a patient about whether or not any of their ancestors or other relative have had a particular disease or disease complication. Such information may be recorded in the set of data items for that patient. The conversion module uses the indication of family history in the set of data items to generate a score for family history of the disease or disease complication. A binary score is given for the family history.

However, the conversion module may also be configured to infer family history from relationships. For example, if the patient data lists the names of parents, grandparents or other relatives, then the database can be searched for the health records of those people, and relevant feature or indicators relating to diseases or disease complications can be extracted to provide scores for those features.

Figure 6:
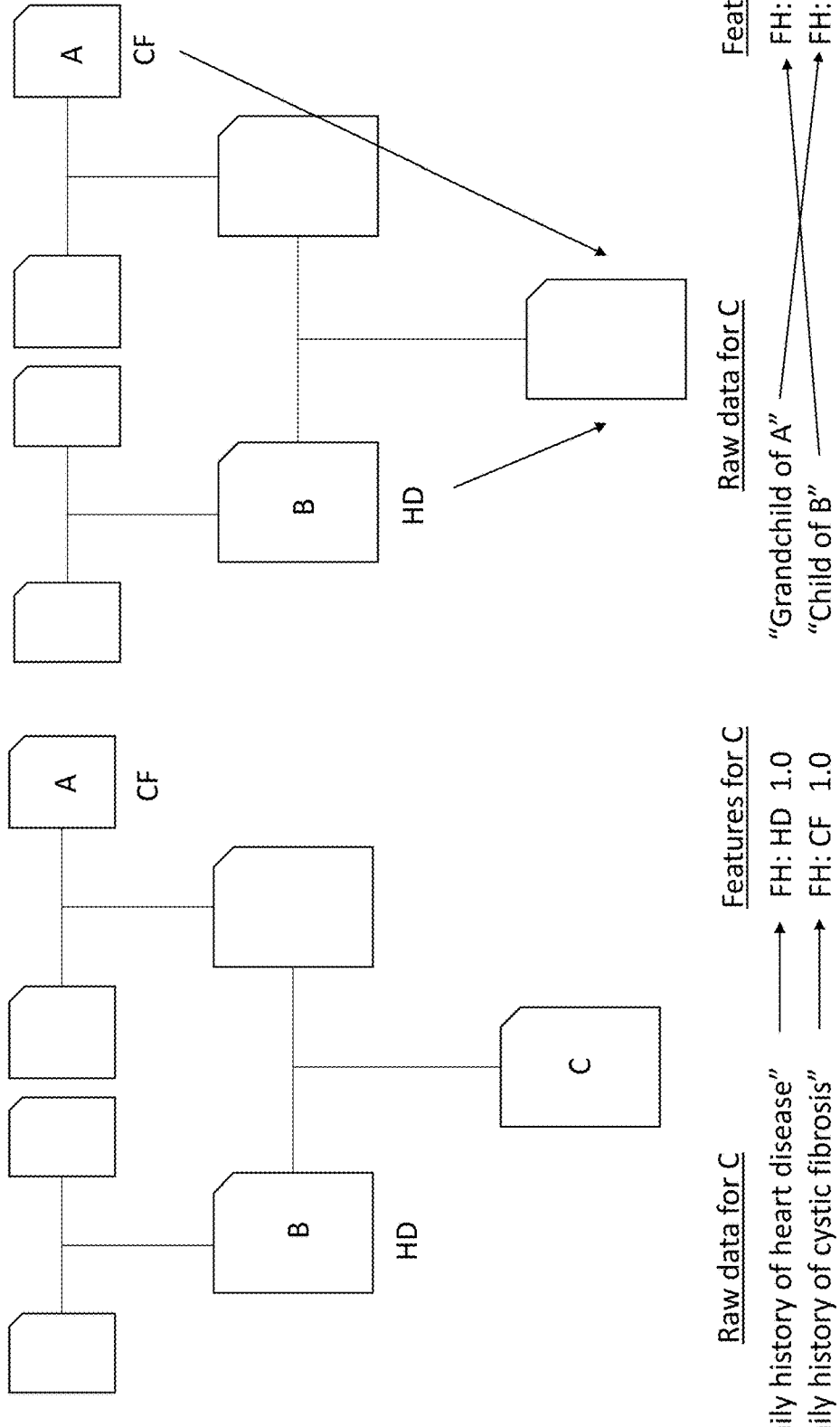
FIG. 6 is a schematic illustration of different options for determining the family history feature scores for a patient.

Reference is made to FIG. 6, which illustrates how the conversion module can determine a score for the family history for a patient. On the left hand side, FIG. 6 illustrates how the family history can be explicitly recorded in a patient's records. On the right hand side, FIG. 6 illustrates how the family history can be inferred in dependence upon relationships recorded in a patient's records.

On the left hand side of the Figure, a family tree of patient 'C' is shown. The family tree shows the parents and grandparents of patient 'C'. One of the parents, labelled person 'B', was diagnosed with heart disease. A record of this is explicitly recorded in the raw health data for patient 'C'. This record is converted to an appropriate data item and used to generate a score representing a family history of heart disease in the feature list (for a training or operating data set) associated with the patient for use with a particular model.

One of the grandparents of patient 'C', labelled person 'A', was diagnosed with cystic fibrosis. A record of this is explicitly recorded in the raw health data for patient 'C'. This record is converted to an appropriate data item and used to generate a score representing a family history of cystic fibrosis in the feature list (for a training or operating data set) associated with the patient for use with a particular model.

On the right hand side of FIG. 6, the same family tree is shown as is shown on the left hand side of FIG. 6. However, in this example, the patient health records do not include explicit records of the family history of disease. However, the raw data used to generate the data items does include indications of the family relationships for patient 'C'. For example the raw data includes a record that patient 'C' is the grandchild of person 'A', and a record that patient 'C' is the child of person 'B'. According to embodiments of the application, these raw data records are used by the system to request health record data associated with person 'A' and person 'B'. The retrieved health record data is then used to determine the family history for patient 'C'. For example, the health record for person 'A' is retrieved by the system and a family history of cystic fibrosis is determined for patient 'C'. The conversion module outputs a score for family history of cystic fibrosis in the feature list based on the inferred history of cystic fibrosis. The health record for person 'B' is retrieved by the system and a family history of heart disease is determined for patient 'C'. The conversion module outputs a score for family history of heart disease in the feature list for patient 'C' based on the inferred history of heart disease.

In some embodiments, the family history data that is recorded may be associated with gender. For example, some inherited diseases may be inherited via the maternal line or paternal line only. Therefore, a feature score may be produced by the conversion module, the feature score indicating a family history of a particular disease along the maternal line. Additionally or alternatively, a feature score may be generated by the conversion module, the feature score indicating a family history of a particular disease along the paternal line. These family history features scores associated with gender may be derived from the raw data using either an explicit record of the gender specific family history (e.g. as shown on the left hand side of FIG. 6) or may be derived by inferred from the raw data containing indications of the family relationships (e.g. as shown on the right hand side of FIG. 6).

Scores for use in a training data set may be generated in a number of different ways. The scores are generated using data input transformations, which are implemented by the conversion module shown in FIG. 1. Some of these data input transformations (such as a decay function) have already been discussed above, but are discussed in more detail below.

One way of generating a score is to utilise a decay function. Each of the data items associated with each person is associated with at least one time (i.e. the onset time, discussed above). A search may be done to collect all data items having a common descriptor to generate a time related description of the behaviour of that particular feature or indicator. Then a score may be assigned based on the history for that descriptor. For example, if a patient recorded abdominal pain one year previously, and there has been no further record of that abdominal pain, the score for abdominal pain, when the training data set is established would be low. If, however, abdominal pain has only recently been recorded and has been noted at the last three recent surgery visits (or other occasions where data has been recorded), then the score may be higher. Scores may be generated on any appropriate scale depending on the feature or indicator that is being scored. Different decay functions may be used for different features or indicators. The aim of the score is to give an indication of the likely weight that should be applied to this particular indicator for this particular patient when the training is performed. An example of the use of a decay function is an impact function in which the contribution to the score for that data item is weighted in dependence upon the amount of time ago the data item was recorded. The score is the result of adding the contributions from the data items weighted in dependence upon the time at which they were recorded. When calculating scores using an impact function, the weighting in dependence upon the amount of time ago the data item was recorded may only be performed for data items recorded more than a predefined time period apart (e.g. 3 days apart).

When a decay function is applied, each data item affecting the score is associated with a weight. The contribution of a data item to the score is dependent upon the weight. The score may be calculated according to:

$$\text{Score} = \sum_i W_i S_i$$

where $S_i$ is the baseline contribution to the score from the $i^{th}$ data item. The baseline contribution to the score for each data item is adjusted by its respective weight, $W_i$.

Figure 8:
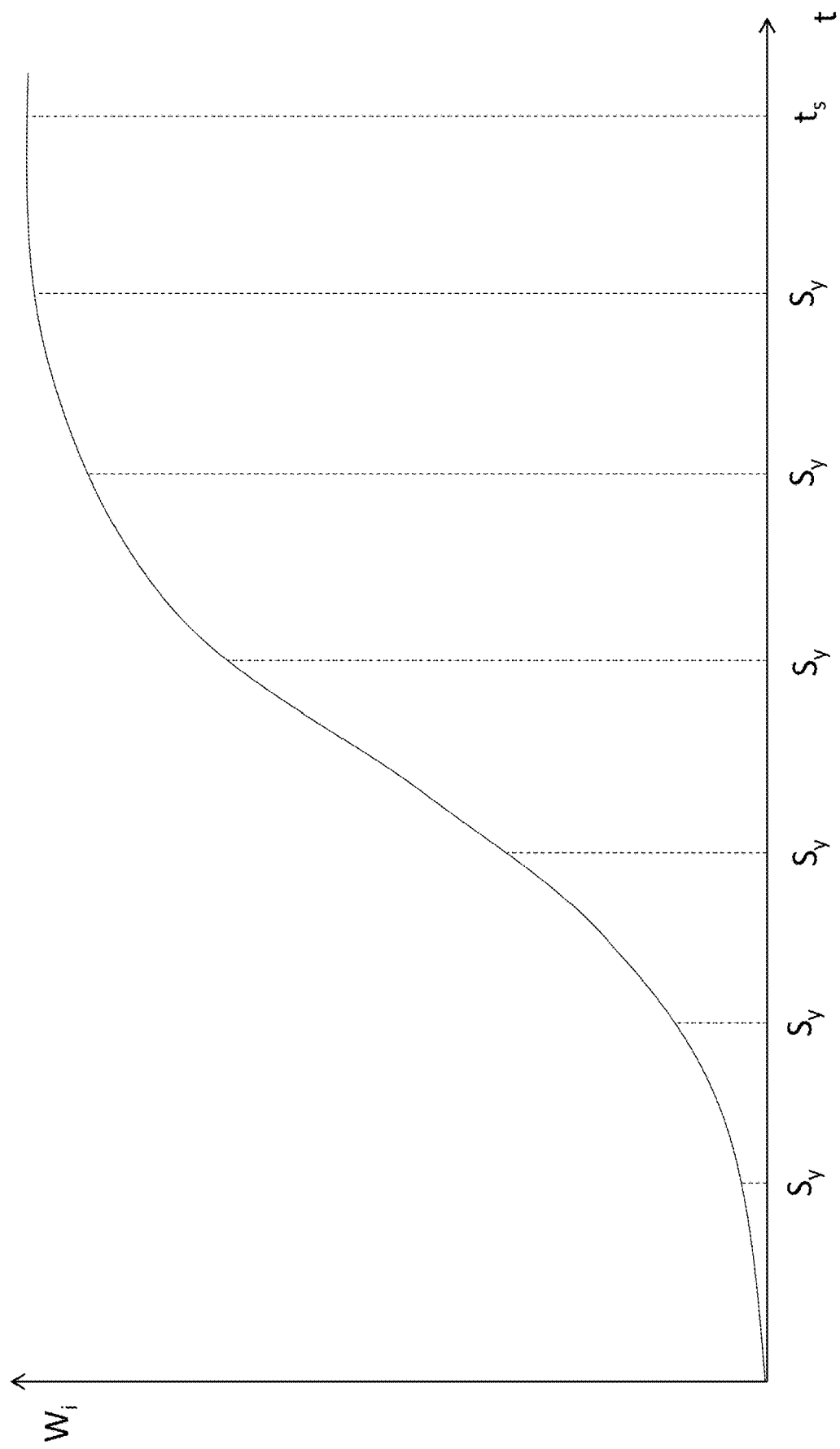
FIG. 8 is an example illustration of how the different symptom records contribute to a feature score in a training data set over time when a decay function is applied.

FIG. 8 illustrates an example of how, when a decay function is applied, the weight varies over time. The time at which the feature score for the training data set is generated is shown at $t_s$. The data items are shown at $S_y$. Each of these may be a record of a symptom, e.g. abdominal pain. In such a case, the score produced from each of the data items would be a score for abdominal pain.

As shown in FIG. 8, the weights for each data item decrease with the difference between the score generation time $t_s$ and the onset time. In other words, "older" data items are weighted less heavily in the calculation of the score, and "younger" (more recent) data items are weighted more heavily. The weights may vary according to a sigmoid function of the onset time, as shown in FIG. 8.

The result of the weighting of data items illustrated by FIG. 8 is that a calculated score associated with a feature will be lower if the relevant data items occurred longer ago in the past.

The width of the sigmoid may vary depending on the symptom to which the decay function is applied.

Another way of generating a score is to generate an average of values which have been reported over a time period. For example, if a column in the training data set relates to smoking, and the patient has reported different number of cigarettes being smoked per day at different times in their history, an aggregate number can be recorded as the score. The aggregate number could, for example, be an average or a mean, or any other statistical representation of the individually reported numbers. One possibility is a rolling mean of previously collected values. Such a rolling mean may be applied to determine a score associated with blood test values.

The conversion module also applies categorisation to determine the scores for a particular patient. For example, each data item may be placed into a category depending upon a value for a feature that it represents. A statistical operation (e.g. averaging or determining standard deviation) is then performed to the categorisation values to obtain a score for the feature. This technique can be applied to determine a score for smoking. In this case, the data items are categorised into different categories (e.g. heavy smoker, moderate smoker, light smoker) according to predetermined rules. A numeric value is associated with each category and is assigned for each data item in that category. The average of the numeric values for each data item is determined and used to provide a score for a patient. The standard deviation of the determined numeric values may also be determined and used for determining the score for the patient.

Figure 9:
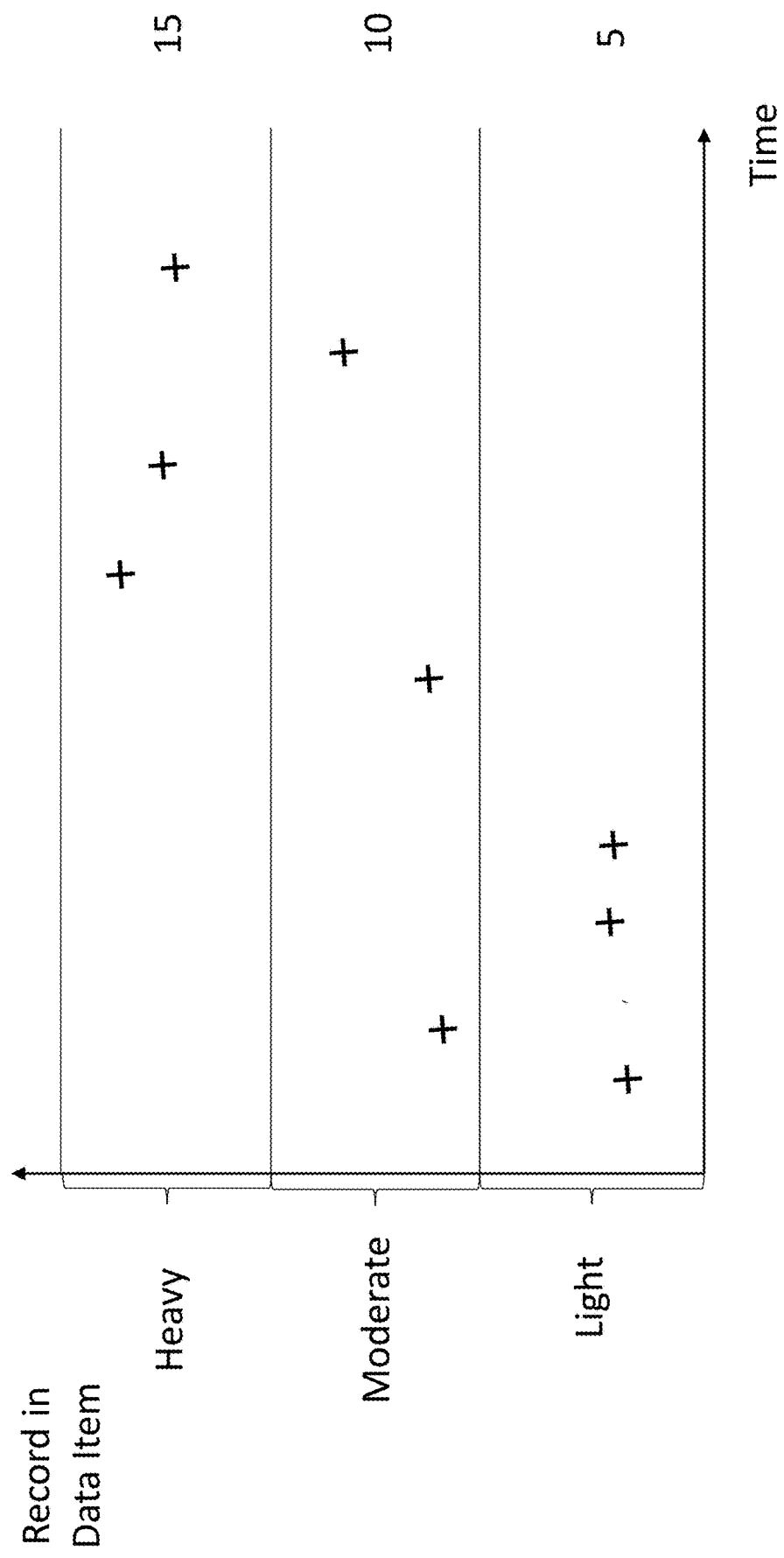
FIG. 9 is an example illustration of how data items are categorised to determine a feature score in a training data set.

Reference is made to FIG. 9, which illustrates the categorisation of the data items for determining a score. Each data item may comprise an indication of the number of cigarettes smoked per week by a patient. Each of the data items is categorised in dependence upon the respective number into one of three categories, i.e. light smoker, moderate smoker, and heavy smoker. Each category is associated with a different number, and therefore a number is associated with each data item. The conversion module averages the numbers for each data item to produce a score for the patient.

In the example shown in FIG. 9, the heavy smoker category is associated with a score of 15, the moderate smoker category is associated with a score of 10, and the light smoker category is associated with a score of 5. Since there are three data items falling within each category, the mean value associated with the values is 10. The conversion module outputs this value as the feature score for the feature 'smoking'.

Although in FIG. 9, there are only three categories, each of which reflects the smoking behaviour of the patient at the time of recordal of the raw data item, in other examples, there may be additional categories, which relate to past behaviour of the patient. For example, there may be categories, such as heavy, moderate, light past smoker, where the data item records historical smoking behaviour reported by the patient.

In some example embodiments, in addition to the use of categories applied to data items to obtain a feature score, a decay function may also be applied to weight each data item, such that older data items are weighted less heavily. Therefore, the average that is obtained to represent the feature score is a weighted average, where the category scores associated with older data items are weighted less heavily when determining the weighted average of the category scores associated with all data items.

Although FIG. 9 presents the categorisation technique in the context of smoking, this technique of categorising and then providing a statistical representation could also be used for calculating scores associated with other features, such as alcohol consumption.

Another way of generating the score is to use a binary score for indicators which are either present or not present. For example, a family history of the particular disease for which the training data set is to be established is scored by 1 or 0 for a patient, regardless of the number of times a family history of the disease appears in the set of data items for that patient. For example, a person either has a family history of ovarian cancer or they do not, and a score associated with a family history of ovarian cancer will be set to either 1 or 0.

In some embodiments, in determining which of two binary values the score takes, the conversion module only takes into account data items having an onset time that is less than a certain time ago. For example, a particular symptom in the training data set may be scored by one if the symptom occurred within the last six months, but scored with zero if the symptom did not occur within the last six months.

In some embodiments, in determining which of two binary values the score takes, the conversion module only takes into account data items having an onset time that is more than a certain time period from a certain diagnosis. For example, when applying a model to determine a patient's probability of appendicitis, a particular symptom (e.g. abdominal pain) may be scored by zero if the symptom occurred within a certain time period of a diagnosis of gastroenteritis, but scored by one if it occurred outside a certain time period of the diagnosis of gastroenteritis.

In some embodiments, in determining which of two binary value the score takes, the conversion module only takes into account data items having an onset time at which the patient is over a certain age. For example, in determining which of two values a binary score takes, a data item indicating menopause is only taken into account if the onset time for the data item indicates that the patient was over 55.

In some embodiments, in determining which of two binary values the score takes, the conversion module determines whether or not the data items include a value for a particular property that falls within a certain range.

In some embodiments, a score may not be truly binary, but may be equal to half the maximum possible value if the onset time of the data item is less than a certain time ago. For example, a particular symptom in the training data set may be scored by one if there is a data item indicating that the symptom occurred within the last six months, scored with 0.5 if there is a data item indicating that the symptom occurred more than six months, and scored with 0 if there is no data item indicating the symptom.

Another type of data input transformation performed by the conversion module for determining the score is to determine the score based on the total number of data items having a particular indicator effective within a certain time period. For example, in determining a score for abdominal pain, the conversion module may determine that there are three data items indicating abdominal pain that have onset times within the last year. The conversion module then outputs a score of 3 for abdominal pain based on these three data items. Even if the set of data items comprises further data items indicating abdominal pain with an onset time outside the last year, these are not taken into account by the conversion module in determining the score.

Another technique for generating a score that is performed by the conversion module is to determine the score in dependence upon the amount of time elapsed since the onset time of the data item. For example, in determining a score associated with diabetes, the number of years since the patient was diagnosed with diabetes may be used to determine the score for input to a model.

Another technique for generating a score that is performed by the conversion module is to determine the score in dependence upon the age of the patient when a particular feature for that patient was recorded. For example, a diagnosis of chicken pox indicated by a data item, may be more heavily weighted and translated into a higher score for a patient if it occurred at a later age. In some embodiments, a lower bound for age may be applied below which recorded data items are not taken into account when evaluating a score. For example, in the case of determining a score for pregnancy, the conversion module may not consider data items indicating pregnancy recorded when the patient had an age below a certain lower bound.

Another technique for generating a score that is performed by the conversion module is to determine the score in dependence upon the most recent data item (i.e. having the most recent onset time) for a feature. For example, if a series of data items for a patient indicate the breathlessness level for a patient, the score for breathlessness may be determined based on the most recent record, with the other data items indicating breathlessness being disregarded when determining the score.

When determining the score for breathlessness, the conversion module may transfer the data items into fake numeric scores. For example, a data item comprising the descriptor "MRC breathlessness scale: 1" would translate into a score of a one for breathlessness (if this data item is the most recent for breathlessness). Similarly, a data item comprising the descriptor "MRC breathlessness scale: 2" would translate into a score of a two for breathlessness (if this data item is the most recent for breathlessness).

Another technique for generating a score that is performed by the conversion module is to determine the score in dependence upon the rate of change of a numeric value indicating by a series of data items. For example, the conversion module may determine a score indicating the rate of change of blood pressure in dependence a plurality of data items, each comprising a descriptor for blood pressure.

The scoring may take into account the number of times a particular feature indicator appears in the set of data items for a patient, the time and frequency with which it appeared and how it was recorded. For example, more weight may be given to a feature or indicator which has been recorded by a doctor or other medical establishment, as opposed to being self-recorded by a patient or user. How the feature was recorded may be determined based on an indication of the location recorded present in the data item, or may be part of the descriptor in the data item.

As mentioned above, each score may be generated in a manner particular to the feature or indicator that it is scoring. For some machine learning models, there is a need, therefore, to normalise the scores and possibly to perform other statistical manipulations common to establishing training data sets. For example, obvious errors or outliers may be removed. Furthermore, features based on a very low information content (i.e. where the number of data items relating to that feature is small) may also be removed, even after that column has been established as a column of the training data set. Normalising training data sets for machine learning models may be carried out in a manner known to a skilled person.

The training data sets that have been generated by the conversion module may be updated by the conversion module. The scores in one or more training data sets may be updated in dependence upon additional data items being received at the conversion module. For example, as new data items describing e.g. new symptoms, treatments performed, are generated and added to the sets of data items associated with the patients that are used to generate a training data set, these new data items are used by the conversion module to update the scores. Furthermore, in the case in which the scores are time dependent—e.g. where the scores are dependent upon the time since the onset time of each data item (e.g. in the example of a decay function)—the scores in the training data set may be updated in response to time elapsing, i.e. the ageing of the data items. The labels in the training data set may also be updated.

Therefore, a new updated training data set for a model may be produced by the conversion module. This may be produced using new relevant data items. A training data set produced six months ago may be updated by the conversion module. The conversion module may receive new data items comprising features recorded in the past six months and use these new data items to update the relevant scores in the training data set.

The update to the training data set may be performed by applying any of the data input transformations described herein using the new data items. For example, conversion module may update a running average for a feature by taking into account the newly recorded data items.

An updated training data set produced by the conversion module may then be applied to retrain the relevant model. The updated one or more training data sets including updated scores and any updated labels are provided to the model to update the relevant one or more machine learning models.

An updated training data set may comprises scores for new features. New data items may become available or be determined to be relevant. In this case, a new feature may be added to produce an update training data set. The updated training data set is then applied to train a new machine learning model, where the new machine learning model has an additional input value with respect to the original machine learning model.

Scores for use in an operating data set may be generated in a number of different ways. The scores are generated using data input transformations, which are implemented by the conversion module shown in FIG. 1A. Some of these data input transformations (such as a decay function) have already been discussed above, but are discussed in more detail below.

One way of generating a score is to utilise a decay function. Each of the data items associated with each person is associated with at least one time (i.e. the onset time, discussed above). A search may be done to collect all data items having a common descriptor to generate a time related description of the behaviour of that particular feature or indicator. Then a score may be assigned based on the history for that descriptor. For example, if a patient recorded abdominal pain one year previously, and there has been no further record of that abdominal pain, the score for abdominal pain, when the operating data set is established would be low. If, however, abdominal pain has only recently been recorded and has been noted at the last three recent surgery visits (or other occasions where data has been recorded), then the score may be higher. Scores may be generated on any appropriate scale depending on the feature or indicator that is being scored. Different decay functions may be used for different features or indicators. The aim of the score is to give an indication of the likely weight that should be applied to this particular indicator for this particular patient when the model is run. An example of the use of a decay function is an impact function in which the contribution to the score for that data item is weighted in dependence upon the amount of time ago the data item was recorded. The score is the result of adding the contributions from the data items weighted in dependence upon the time at which they were recorded. When calculating scores using an impact function, the weighting in dependence upon the amount of time ago the data item was recorded may only be performed for data items recorded more than a predefined time period apart (e.g. 3 days apart).

When a decay function is applied, each data item affecting the score is associated with a weight. The contribution of a data item to the score is dependent upon the weight. The score may be calculated according to:

$$\text{Score} = \sum_i W_i S_i$$

where $S_i$ is the baseline contribution to the score from the $i^{th}$ data item. The baseline contribution to the score for each data item is adjusted by its respective weight, $W_i$.

Figure 11:
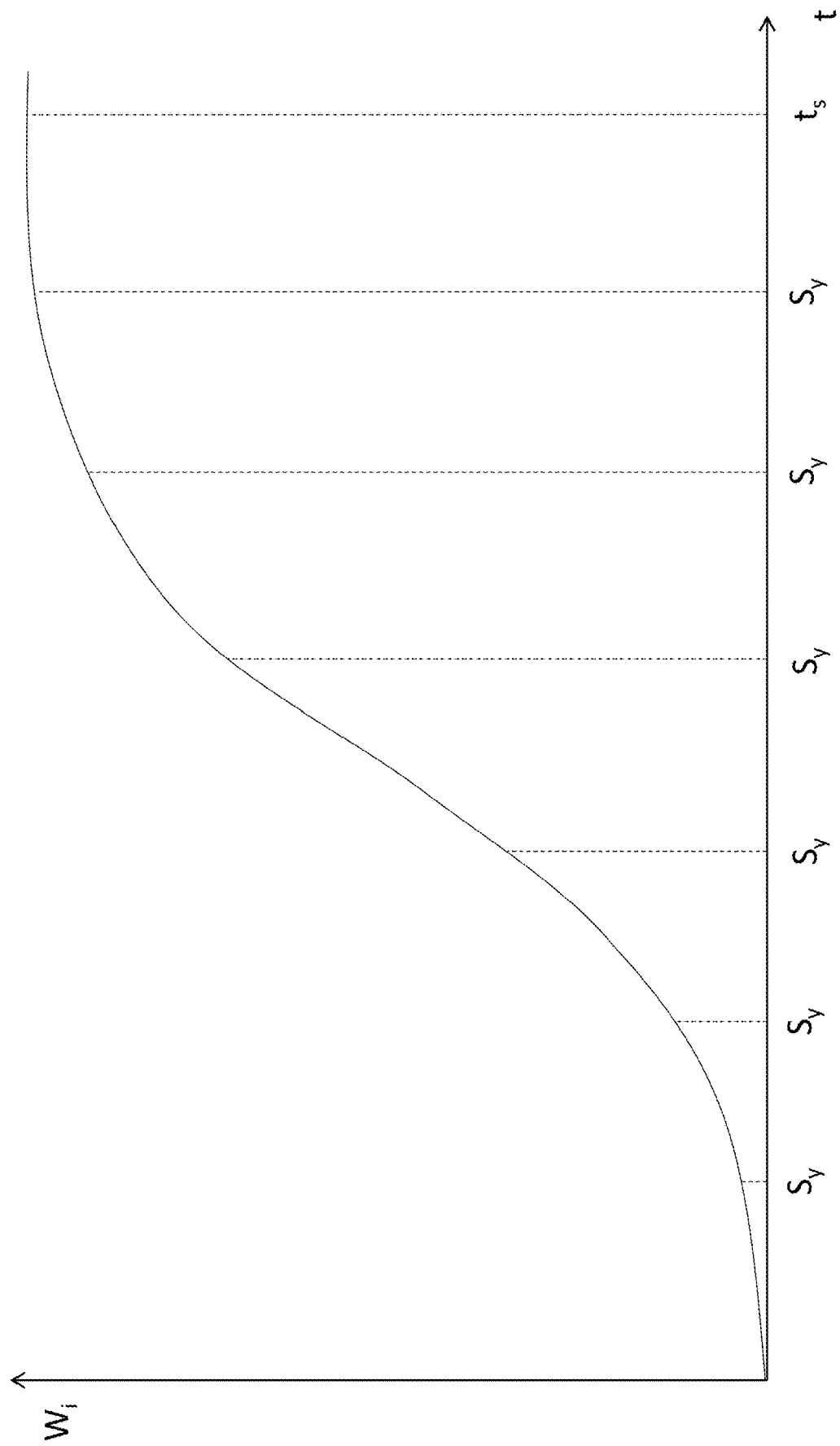
FIG. 11 is an example illustration of how the different symptom records contribute to a feature score in an operating data set over time when a decay function is applied.

FIG. 11 illustrates an example of how, when a decay function is applied, the weight varies over time. The time at which the feature score for the operating data set is generated is shown at $t_s$. The data items are shown at $S_y$. Each of these may be a record of a symptom, e.g. abdominal pain. In such a case, the score produced from each of the data items would be a score for abdominal pain.

As shown in FIG. 11, the weights for each data item decrease with the difference between the score generation time $t_s$ and the onset time. In other words, older data items are weighted less heavily in the calculation of the score, and younger data items are weight more heavily. The weights may vary according to a sigmoid function of the onset time, as shown in FIG. 11.

The result of the weighting of data items illustrated by FIG. 11 is that a calculated score associated with a feature will be lower if the relevant data items occurred longer ago in the past.

Another way of generating a score is to generate an average of values which have been reported over a time period. For example, if a column in the operating data set relates to smoking, and the patient has reported different number of cigarettes being smoked per day at different times in their history, an aggregate number can be recorded as the score. The aggregate number could, for example, be an average or a mean, or any other statistical representation of the individually reported numbers. One possibility is a rolling mean of previously collected values. Such a rolling mean may be applied to determine a score associated with blood test values.

The conversion module also applies categorisation to determine the scores for a particular patient. For example, each data item may be placed into a category depending upon a value for a feature that it represents. A statistical operation (e.g. averaging or determining standard deviation) is then performed to the categorisation values to obtain a score for the feature. This technique can be applied to determine a score for smoking. In this case, the data items are categorised into different categories (e.g. heavy smoker, moderate smoker, light smoker) according to predetermined rules. A numeric value is associated with each category and is assigned for each data item in that category. The average of the numeric values for each data item is determined and used to provide a score for a patient. The standard deviation of the determined numeric values may also be determined and used for determining the score for the patient.

Figure 12:
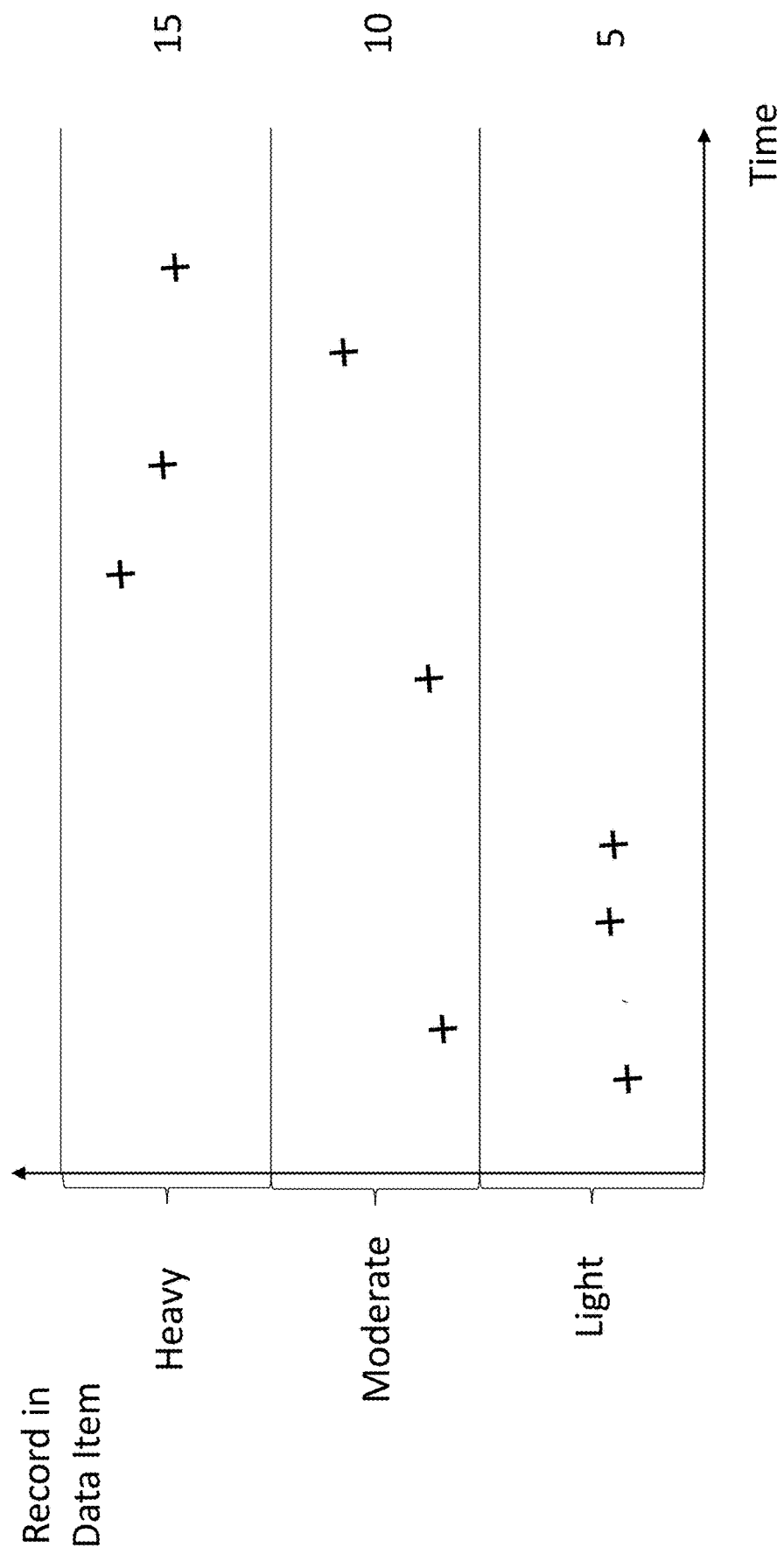
FIG. 12 is an example illustration of how data items are categorised to determine a feature score in an operating data set.

Reference is made to FIG. 12, which illustrates the categorisation of the data items for determining a score. Each data item may comprise an indication of the number of cigarettes smoked per week by a patient. Each of the data items is categorised in dependence upon the respective number into one of three categories, i.e. light smoker, moderate smoker, and heavy smoker. Each category is associated with a different number, and therefore a number is associated with each data item. The conversion module averages the numbers for each data item to produce a score for the patient.

In the example shown in FIG. 12, the heavy smoker category is associated with a score of 15, the moderate smoker category is associated with a score of 10, and the light smoker category is associated with a score of 5. Since there are three data items falling within each category, the mean value associated with the values is 10. The conversion module outputs this value as the feature score for the feature 'smoking'.

Although in FIG. 12, there are only three categories, each of which reflects the smoking behaviour of the patient at the time of recordal of the raw data item, in other examples, there may be additional categories, which relate to past behaviour of the patient. For example, there may be categories, such as heavy, moderate, light past smoker, where the data item records historical smoking behaviour reported by the patient.

In some example embodiments, in addition to the use of categories applied to data items to obtain a feature score, a decay function may also be applied to weight each data item, such that older data items are weighted less heavily. Therefore, the average that is obtained to represent the feature score is a weighted average, where the category scores associated with older data items are weighted less heavily when determining the weighted average of the category scores associated with all data items.

Although FIG. 12 presents the categorisation technique in the context of smoking, this technique of categorising and then providing a statistical representation could also be used for calculating scores associated with other features, such as alcohol consumption.

Another way of generating the score is to use a binary score for indicators which are either present or not present. For example, a family history of the particular disease for which the operating data set is to be established is scored by 1 or 0 for a patient, regardless of the number of times a family history of the disease appears in the set of data items for that patient. For example, a person either has a family history of ovarian cancer or they do not, and a score associated with a family history of ovarian cancer will be set to either 1 or 0.

In some embodiments, in determining which of two binary values the score takes, the conversion module only takes into account data items having an onset time that is less than a certain time ago. For example, a particular symptom in the operating data set may be scored by one if the symptom occurred within the last six months, but scored with zero if the symptom did not occur within the last six months.

In some embodiments, in determining which of two binary values the score takes, the conversion module only takes into account data items having an onset time that is more than a certain time period from a certain diagnosis. For example, when applying a model to determine a patient's probability of appendicitis, a particular symptom (e.g. abdominal pain) may be scored by zero if the symptom occurred within a certain time period of a diagnosis of gastroenteritis, but scored by one if it occurred outside a certain time period of the diagnosis of gastroenteritis.

In some embodiments, in determining which of two binary value the score takes, the conversion module only takes into account data items having an onset time at which the patient is over a certain age. For example, in determining which of two values a binary score takes, a data item indicating menopause is only taken into account if the onset time for the data item indicates that the patient was over 55.

In some embodiments, in determining which of two binary values the score takes, the conversion module determines whether or not the data items include a value for a particular property that falls within a certain range.

In some embodiments, a score may not be truly binary, but may be equal to half the maximum possible value if the onset time of the data item is less than a certain time ago. For example, a particular symptom in the operating data set may be scored by one if there is a data item indicating that the symptom occurred within the last six months, scored with 0.5 if there is a data item indicating that the symptom occurred more than six months, and scored with 0 if there is no data item indicating the symptom.

Another type of data input transformation performed by the conversion module for determining the score is to determine the score based on the total number of data items having a particular indicator effective within a certain time period. For example, in determining a score for abdominal pain, the conversion module may determine that there are three data items indicating abdominal pain that have onset times within the last year. The conversion module then outputs a score of 3 for abdominal pain based on these three data items. Even if the set of data items comprises further data items indicating abdominal pain with an onset time outside the last year, these are not taken into account by the conversion module in determining the score.

Another technique for generating a score that is performed by the conversion module is to determine the score in dependence upon the amount of time elapsed since the onset time of the data item. For example, in determining a score associated with diabetes, the number of years since the patient was diagnosed with diabetes may be used to determine the score for input to a model.

Another technique for generating a score that is performed by the conversion module is to determine the score in dependence upon the age of the patient when a particular feature for that patient was recorded. For example, a diagnosis of chicken pox indicated by a data item, may be more heavily weighted and translated into a higher score for a patient if it occurred at a later age. In some embodiments, a lower bound for age may be applied below which recorded data items are not taken into account when evaluating a score. For example, in the case of determining a score for pregnancy, the conversion module may not consider data items indicating pregnancy recorded when the patient had an age below a certain lower bound.

Another technique for generating a score that is performed by the conversion module is to determine the score in dependence upon the most recent data item (i.e. having the most recent onset time) for a feature. For example, if a series of data items for a patient indicate the breathlessness level for a patient, the score for breathlessness may be determined based on the most recent record, with the other data items indicating breathlessness being disregarded when determining the score.

When determining the score for breathlessness, the conversion module may transfer the data items into fake numeric scores. For example, a data item comprising the descriptor "MRC breathlessness scale: 1" would translate into a score of a one for breathlessness (if this data item is the most recent for breathlessness). Similarly, a data item comprising the descriptor "MRC breathlessness scale: 2" would translate into a score of a two for breathlessness (if this data item is the most recent for breathlessness).

Another technique for generating a score that is performed by the conversion module is to determine the score in dependence upon the rate of change of a numeric value indicating by a series of data items. For example, the conversion module may determine a score indicating the rate of change of blood pressure in dependence a plurality of data items, each comprising a descriptor for blood pressure.

The scoring may take into account the number of times a particular feature indicator appears in the set of data items for a patient, the time and frequency with which it appeared and how it was recorded. For example, more weight may be given to a feature or indicator which has been recorded by a doctor or other medical establishment, as opposed to being self-recorded by a patient or user. How the feature was recorded may be determined based on an indication of the location recorded present in the data item, or may be part of the descriptor in the data item.

In some embodiments, the output of the machine learning model can be further processed in a rule based manner to obtain a result. One way in which this may be achieved is to temporarily set the output from the machine learning model to zero in response to certain conditions being met. In other words, the output from the machine learning model is temporarily suppressed. This is referred to as a 'snooze' function. The snooze function may implemented by the system implementing the machine learning model.

Figure 13:
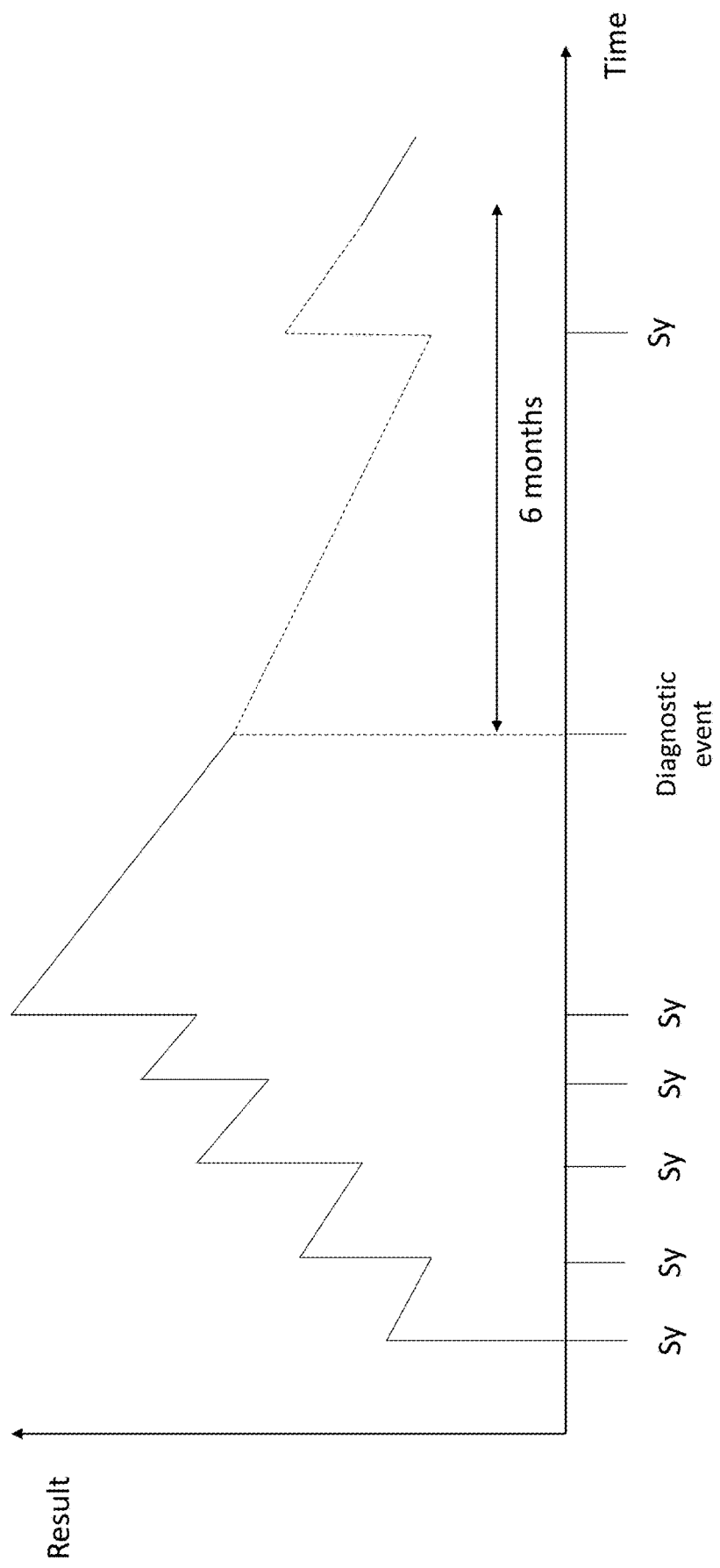
FIG. 13 is an example illustration of how a result obtained from a machine learning model varies over time when a snooze function is applied.

Reference is made to FIG. 13, which illustrates an example of the use of the snooze function applied to the output of a machine learning model. As shown, the result associated with a negative health outcome increases with the number of data items recording a particular symptom. A decay function is applied so that older records of that symptom are weighted less heavily than newer records, and therefore have less impact on the output of the model. The machine learning model may using the feature scores, including the symptom discussed, determine the probability of a patient having ovarian cancer. The results from a diagnostic event, e.g. an ultra sound, indicating that a patient is unlikely to have ovarian cancer may significantly reduce the probability that the symptom is caused by ovarian cancer. Therefore, the result is set to zero for a certain predefined time period, e.g. six months. Therefore, the snooze function sets the result to zero if the relevant diagnostic event was less than the predefined time period ago. If the relevant diagnostic event occurred more than the predefined time period ago, the result may be non-zero again. This allows for the possibility that the diagnosis performed may no longer be an accurate assessment of the current state of the patient. The output after the predefined time period (the snooze period), is determined based on the data items recorded prior to the diagnostic event and any data items recorded after the diagnostic event. Since the data items age whilst the result is zeroed, and hence some of the scores input to the machine learning model decay over time, as shown in FIG. 13, the output of the machine learning model will alter over time changing with the "decayed" features. The output may change at each time the model is run, even if there is no further input and no other changes—that is, time is the only affecting variable. Furthermore, the output is also affected by any further data items that are presented after the diagnostic event whilst the snooze is active. When the snooze function is removed after the predefined time period, the result is the value taken as though the snooze function was never applied.

Figure 14:
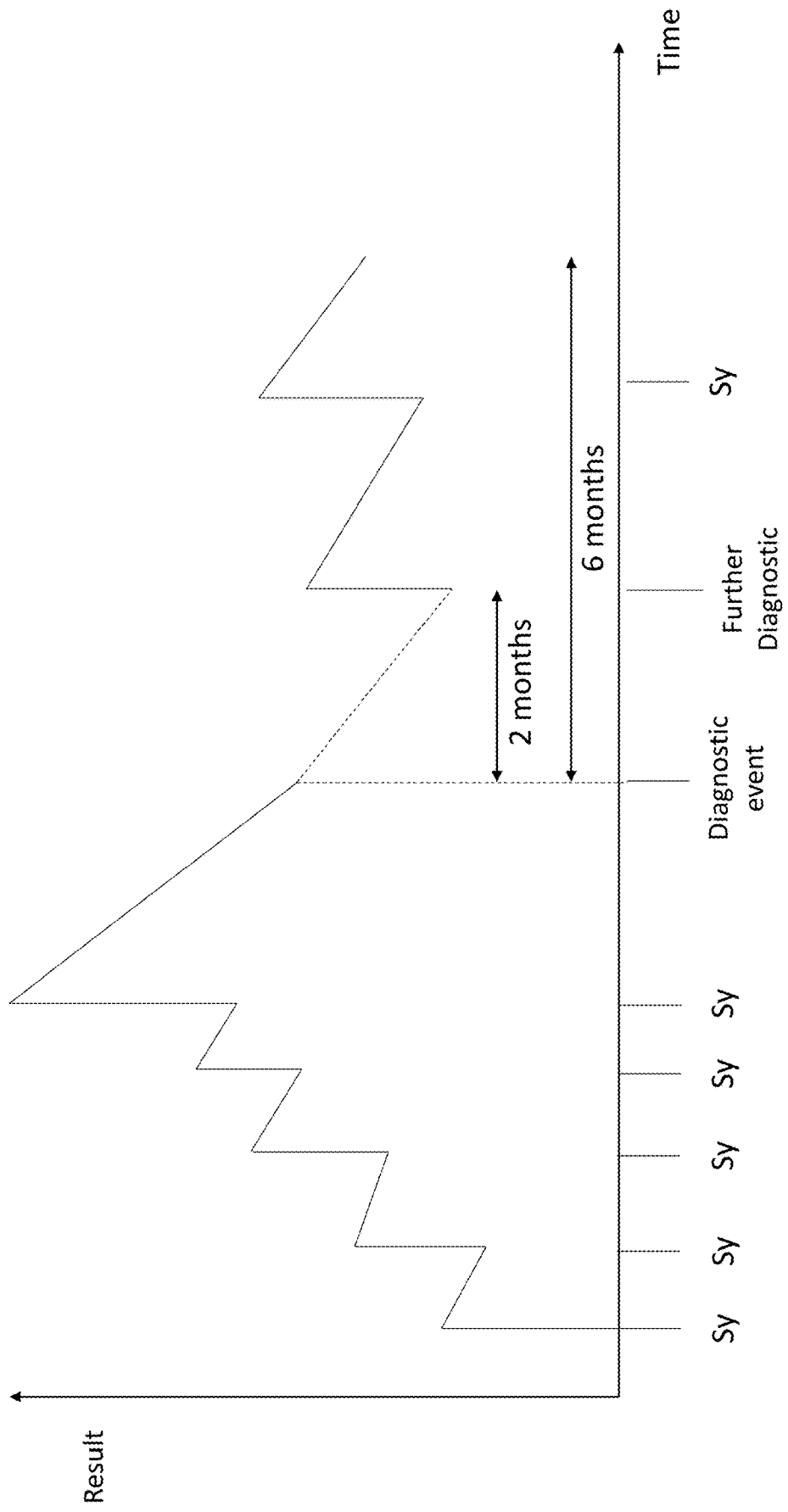
FIG. 14 is an example illustration of how a result obtained from a machine learning model varies over time when a snooze function is applied and a data item indicating a further diagnostic event occurs.

In some examples, the snooze period can be interrupted by a further diagnostic event. Reference is made to FIG. 14, which illustrates an example where, following the occurrence of a diagnostic event, the result from the machine learning model is set to zero. However, at a later time (2 months later, in this example), a further diagnostic event occurs. If the first diagnostic event was an ultrasound indicating that ovarian cancer is unlikely, the second diagnostic event may be a blood test indicating a reasonable probability of ovarian cancer. Therefore, the result obtained from the machine learning model, which was previously set to zero following the first diagnostic event, is then set to a non-zero value again following the second diagnostic event, cutting short the snooze period. The further diagnostic event may also affect a score input to the machine learning model (as shown in FIG. 14) causing a change in the output from the machine learning model and hence a change in the result. The score following the shortened snooze period is dependent upon any decay or further records that would have taken place during the snooze period.

The following description provides an example explanation of machine learning processes that may be used to implement embodiments of the application. Furthermore, a description of the hardware in which embodiments may be implemented is provided.

Machine Learning is a branch of research for enabling computer systems to solve problems and perform tasks without explicit instructions. Machine learning systems autonomously analyse data sets, referred to as 'training data', in order to train mathematical models during a training phase. Once trained on the basis of the training data, the mathematical model is then applied to data sets to make predictions and/or decisions during an operating phase.

There are two distinct types of machine learning, referred to as supervised learning and unsupervised learning. In supervised learning, the training data for constructing the model includes both input data and desired output data. The parameters of the model are tuned on the basis of the input data so as to result in a model that is able to approximately generate the output data from the input data. The output data typically comprises a set of labels that have been provided by humans to label the sets of input data.

Supervised learning may be used to perform classification of input data into a particular category. For example, a mathematical model that is trained to perform optical character recognition may, when provided with data representing an image of a letter of the alphabet, output an indication of the one of the 26 different letters of the alphabet that is shown in the image. This type of model is referred to as a classifier model, since the image is classified into one of a set of categories (i.e. letters of the alphabet). Another type of supervised learning model may be used to perform regression analysis of input data. In this case, the output data comprises one or more continuous values rather than a discrete class. For example, a mathematical model may be trained to output an estimate for the value of a property given a set of input data, including location, size, age, etc.

In unsupervised learning, the training data for constructing the model includes input data, but does not include labels or outputs of the model. Instead of training the model to reproduce the output data from the input data, in unsupervised learning, the model is trained on the basis of commonalities in the training data and provides outputs based on the presence or absence of those commonalities in the future input data. Unsupervised learning has applications in dimensionality reduction and in cluster analysis.

One type of model widely used in the field of machine learning is the artificial neural network. Neural networks comprise arrangements of sets of nodes which are interconnected by links and which interact with each other. The principles of neural networks in computing are based on information about how electrical stimuli convey information in the human brain. For this reason, the nodes are often referred to as neurons. They may also be referred to as vertices. The links are sometimes referred to as edges. The network can take input data and certain nodes perform operations on the data. The result of these operations is passed to other nodes. The output of each node is referred to as its activation or node value. Each link is associated with a weight. A weight defines the connectivity between nodes of the neural network. Many different techniques are known by which neural networks are capable of learning, which takes place by altering values of the weights.

Figure 15:
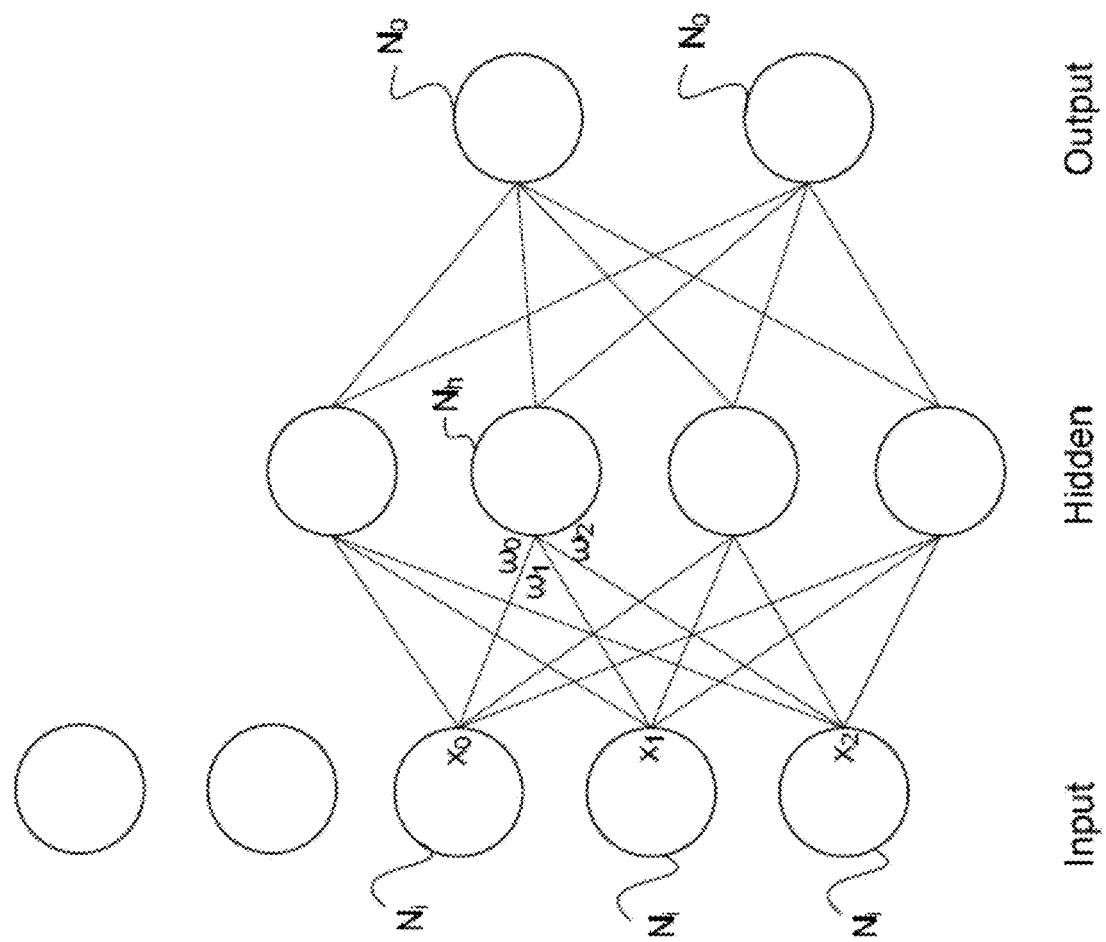
FIG. 15 is a simplified schematic view of a neural network.
Figure 16:
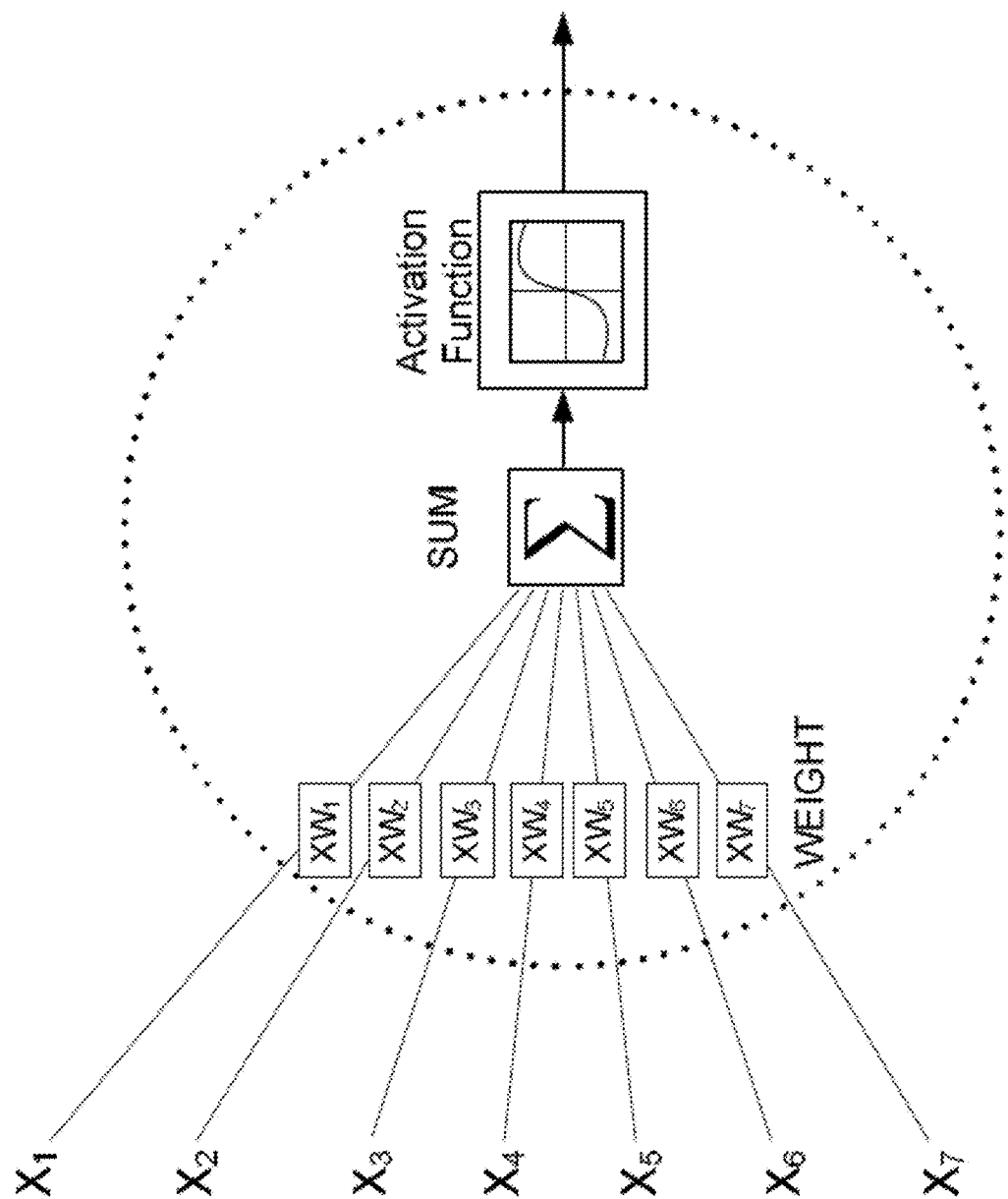
FIG. 16 is a simplified schematic view of a neuron.

FIG. 15 shows an extremely simplified version of one arrangement of nodes in a neural network. This type of arrangement is often used in learning or training and comprises an input layer of nodes, a hidden layer of nodes and an output layer of nodes. In reality, there will be many nodes in each layer, and nowadays there may be more than one layer per section. Each node of the input layer Ni is capable of producing at its output an activation or node value which is generated by carrying out a function on data provided to that node. A vector of node values from the input layer is scaled by a vector of respective weights at the input of each node in the hidden layer, each weight defining the connectivity of that particular node with its connected node in the hidden layer. In practice, networks may have millions of nodes and be connected multi-dimensionally, so the vector is more often a tensor. The weights applied at the inputs of the node Nh are labelled w0 . . . w2. Each node in the input layer is connected at least initially to each node in the hidden layer. Each node in the hidden layer can perform an activation function on the data which is provided to them and can generate similarly an output vector which is supplied to each of the nodes $N_O$ in the output layer $N_O$. Each node weights its incoming data, for example by carrying out the dot product of the input activations of the node and its unique weights for the respective incoming links. It then performs an activation function on the weighted data. The activation function can be for example a sigmoid. See FIG. 16. The network learns by operating on data input at the input layer, assigning weights to the activations from each node and acting on the data input to each node in the hidden layer (by weighting it and performing the activation function). Thus, the nodes in the hidden layer operate on the weighted data and supply outputs to the nodes in the output layer. Nodes of the output layer may also assign weights. Each weight is characterised by a respective error value. Moreover, each node may be associated with an error condition. The error condition at each node gives a measure of whether the error in the weight of the node falls below a certain level or degree of acceptability. There are different learning approaches, but in each case there is a forward propagation through the network from left to right in FIG. 15, a calculation of overall error, and a backward propagation from right to left in FIG. 15 through the network of the error. In the next cycle, each node takes into account the back-propagated error and produces a revised set of weights. In this way, the network can be trained to perform its desired operation.

Different types of neural network are known. One type of neural network is a feedforward neural network, in which the information in the network travels through the network in only one direction from the input layer to the output layer. In each case, the activation of the next layer depends upon the activation of the previous layer and the weights of the connections between the two layers. Feed forward neural networks can be time aware, in which case, the activation of a particular node is dependent upon time values associated with the input data. Another type of neural network is a recurrent neural network, in which, outputs from nodes of the neural networks are provided as inputs to earlier nodes in the neural network. This may be performed by providing the outputs of the neural network as inputs to the neural network. Alternatively, this may be performed by nodes in the hidden layer/s of the network receiving as inputs, their previous output from one or more iterations prior to their current iteration. A special type of recurrent neural network is a Long Short Term Memory (LSTM) neural network, in which nodes retain information for longer periods of time and are, therefore, capable of processing data having time gaps.

Figure 17:
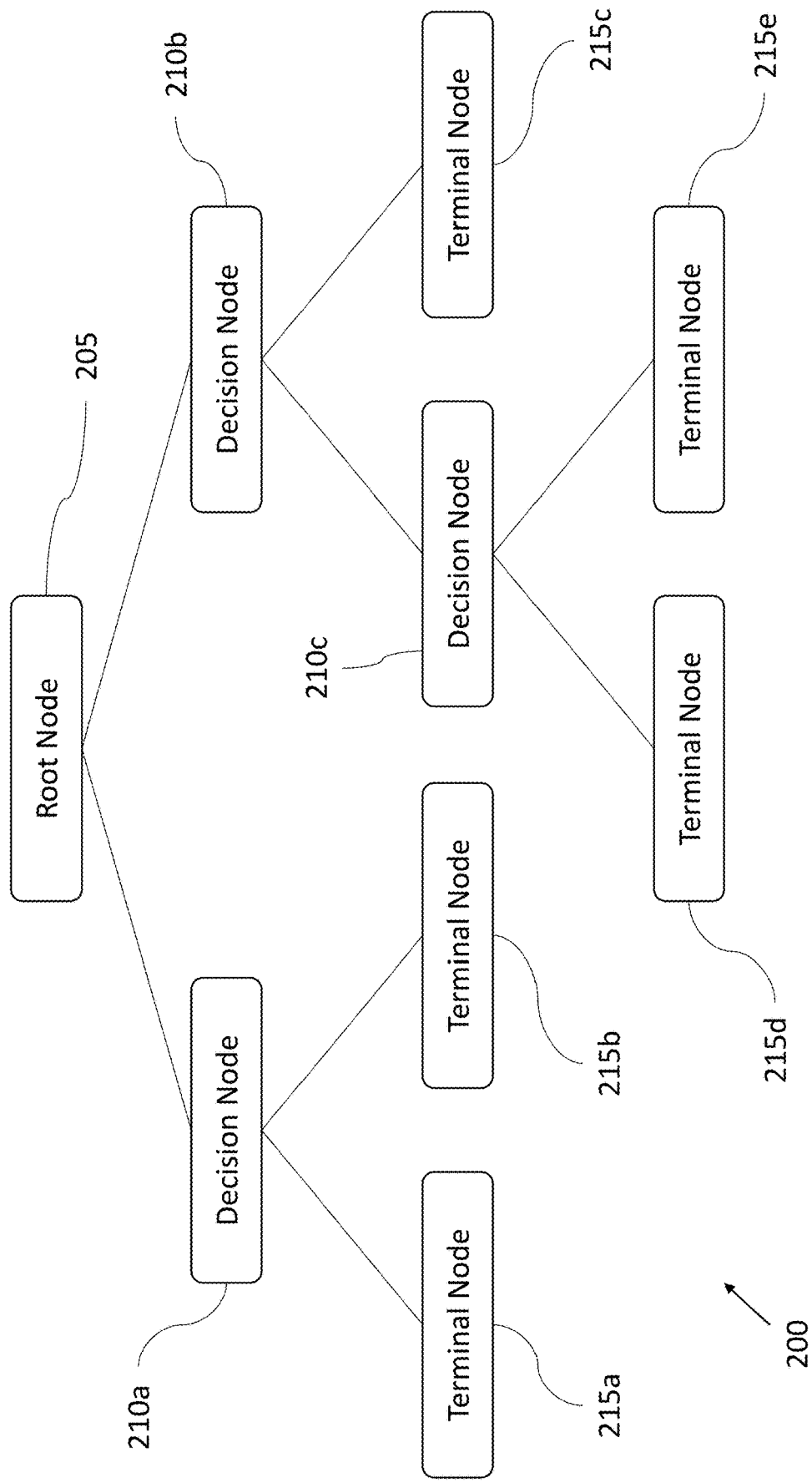
FIG. 17 is a simplified schematic view of decision tree.

Other than neural networks, another model that may be used for performing machine learning is a decision tree. A decision tree is an example of a supervised machine learning model. Reference is made to FIG. 17, which illustrates an example of a decision tree 200. The decision tree 200 comprises a series of nodes. During the operating phase, input data is provided to the top of the decision tree, and decisions are made on the basis of the data to reach a certain output at the bottom of the tree. The decision tree 200 comprises a root node 205, which represents the start of the decision tree. At the root node 205 a decision is made on the basis of every set of input data fed into the tree, as to which branch of the tree to proceed down for that set of data. The decision made for a first set of data at the root node 205 may cause the decision process to proceed to decision node 210*a*. On the other hand, a decision made for a second set of data at the root node 205 may cause the decision process to proceed to decision node 210*b*.

When the process has proceeded to one of the decision nodes 210*a*, 210*b*, a decision associated with the particular decision node is then made by applying certain criteria to the set of input data. This decision is then used to determine the next node in the decision tree, to which the process proceeds. This next node may be a further decision node, such as decision node 210*c* or it may be a terminal node (i.e. a leave), such as terminal nodes 215*a*, 215*b*, 215*c*, 215*d*, 215*e*. Each of the terminal nodes represents an output or target value of the decision tree. Hence, by making decisions based on the input values at the root node 205 and each subsequent decision node, the model eventually identifies a terminal node and corresponding output. Hence, decision trees can be used to produce an output from one or more input values.

One type of decision tree is a classification tree, which classifies the one or more input values into a discrete category. Another type of decision tree is a regression tree, where the target variable changes continuously with the input values.

Therefore, as described, a decision tree may be used, during an operating phase, to output a classification and/or a continuous value in dependence upon the input value. During the training phase, the decision tree can be trained by splitting the input data into different subsets based on the values in the input data. The process is repeated on each subset in a recursive manner, until either the data points in a subset at a node in the tree all have the same value for the output or when splitting no longer adds value to the predictions. Once a decision tree is trained, it is then applied to new input data, during an operating phase, to determine previously unknown results.

One limitation present in the use of such decision trees, is their tendency to overfit to the data used to train them. Partitioning the data into subsets until all of the data points correspond to the same output, overfits to the training data, such that poor predictions for future input data sets during the operating phase may result. To overcome this limitation a technique known as a random forest may be applied. A random forest involves, during the training phase, constructing a plurality of decision trees using randomly selected different subsets of the input data. During the operating phase, the same input is provided to each of the decision trees. In the case of classification, the output from the random forest is the mode of the outputs from each of the individual decision trees. On the other hand, in the case of regression analysis, the output from the random forest is the mean of the outputs from each of the individual decision trees. Applying this random forest, where the outputs from a plurality of decision trees are averaged, addresses the problem of overfitting to the data.

Another type of model that may be used for machine learning is a clustering algorithm, such as the k-mean clustering algorithm. This is a type of unsupervised machine learning, which is used to assign different data points into different groups. The algorithm iteratively assigns each data point to one of k groups based on the features that are provided.

Figure 18:
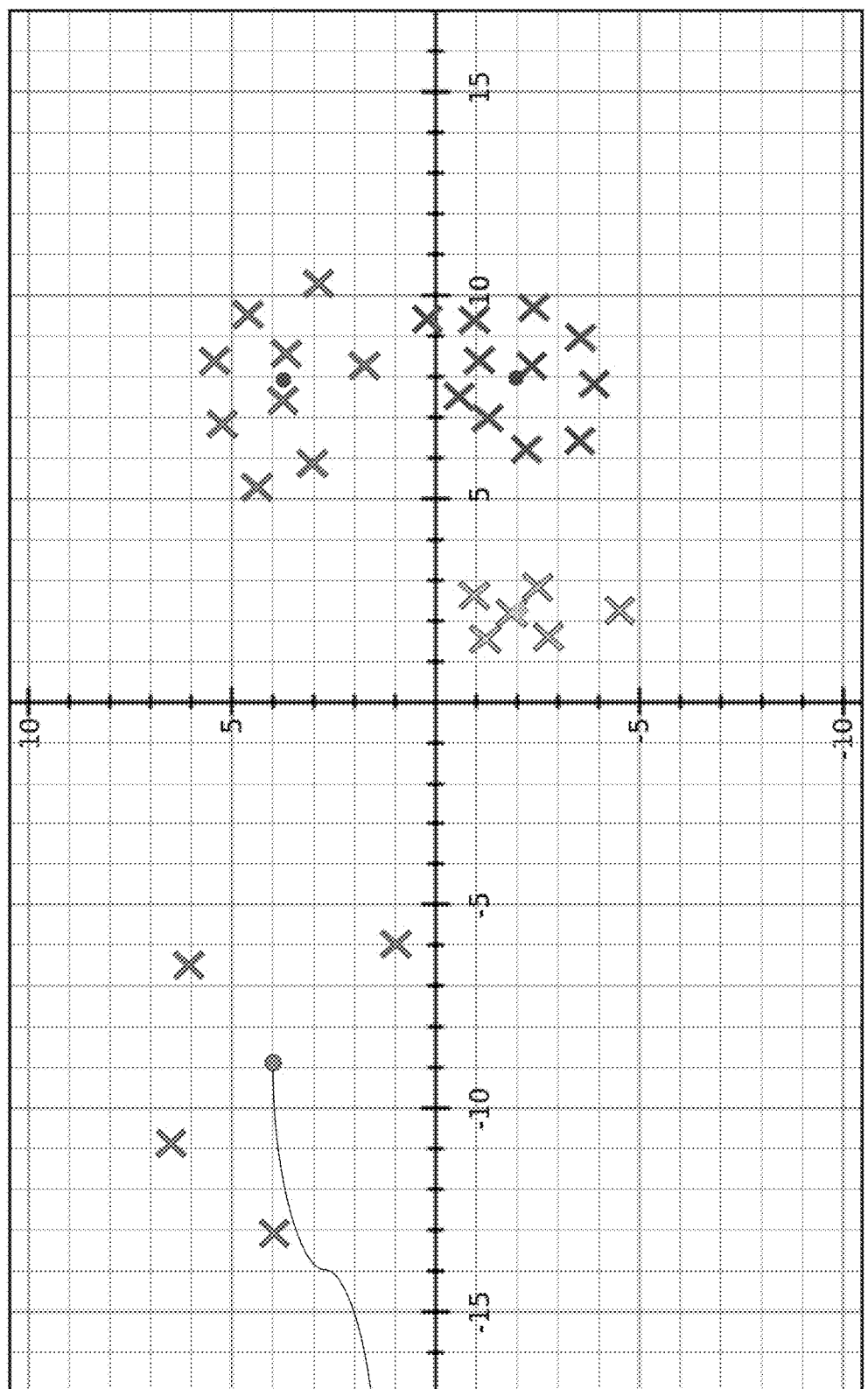
FIG. 18 is an example illustration of clustering of data point using a machine learning model.

Reference is made to FIG. 18, which illustrates a set of data points that are grouped into four different clusters (i.e. k=4). In this example, each data point comprises two variables and is shown as being represented at a position in 2-dimensional space. Each cluster has an associated centroid, which represents the mean position for each cluster. For example, for the cluster present in the top left quadrant of the 2-dimensional space, the centroid 290 is defined for that cluster.

Initially, before the clustering algorithm is applied, all of the data points are unassigned to any one of the clusters. A centroid is first defined for each of the four clusters. Each centroid may be defined by randomly selecting a data point from the set of data points or may be randomly generated without reference to the set of data points. The remaining data points are then each assigned to one of the four clusters. Each data point is in turn assigned to the cluster for which the squared Euclidean distance between the centroid for that cluster and the data point is minimised. Each time a data point is added to a cluster, the position of the centroid for that cluster is updated to reflect the new mean for the cluster. Eventually, all of the data points are assigned to one of the k clusters.

By applying such a clustering algorithm, a model can be applied to categorise data in an unsupervised manner.

Figure 19:
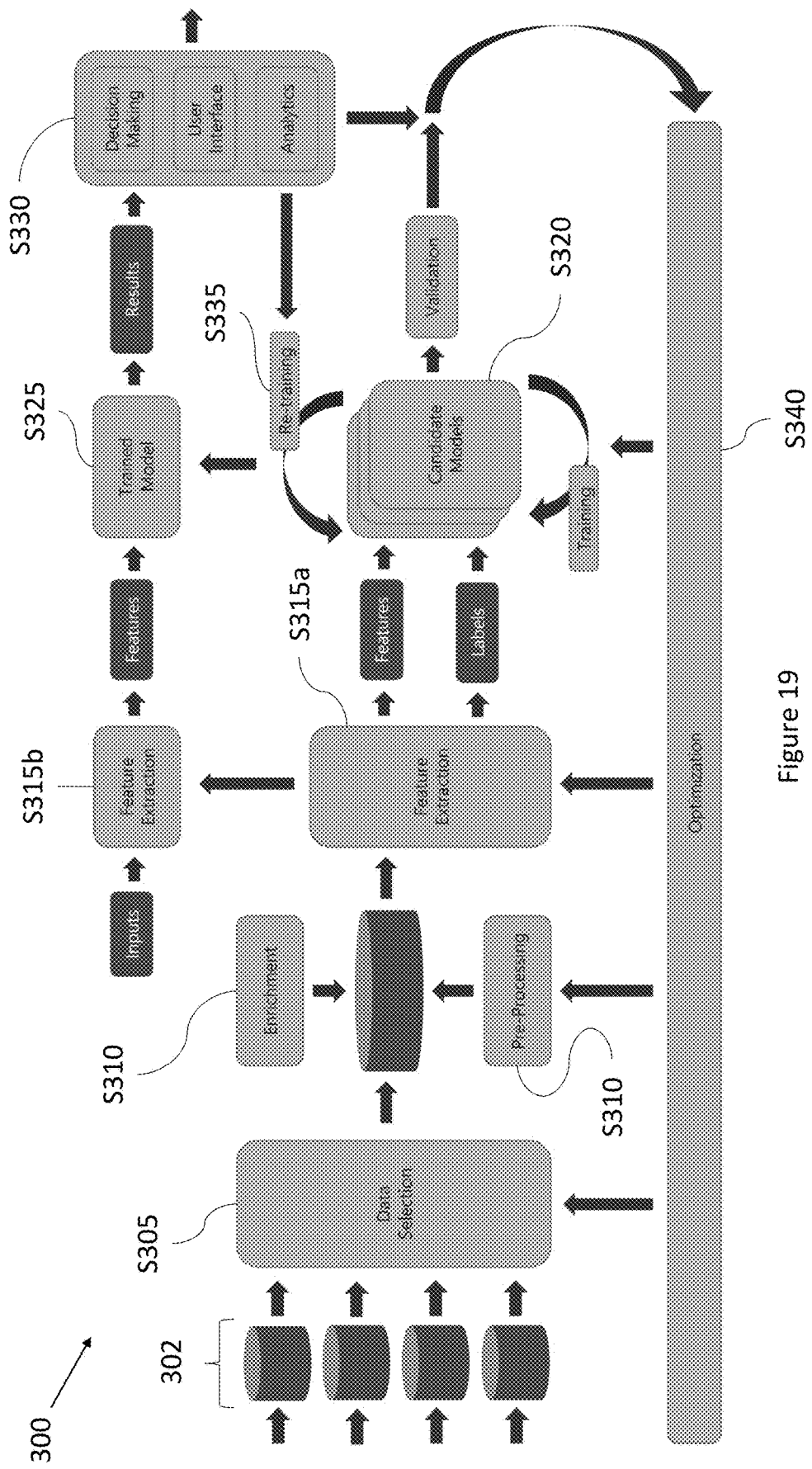
FIG. 19 is a schematic view of the process for training and operating machine learning models.

Reference is made to FIG. 19, which illustrates an overall process 300 by which machine learning can be applied to analyse data. The Figure illustrates one or more data sources 302, which could be, for example, one or more databases storing patient records. At S305 data is selected from the one or more data sources 302. The data selection is carried out in dependence upon the particular request that is being carried out. For example, a certain set of data may be extracted for analysing the cardiovascular risk for a patient. A different set of data may be extracted for detecting ovarian cancer for a patient.

At S310, the selected data is enriched and pre-processed. Enriching the data comprises augmenting the raw data with further information. This information may allow for the data to be interpreted and converted to a standard format. This information may be provided on demand. For example, based on the received raw data, the system determines that further information is required for providing to the machine learning model. This further information can be retrieved and applied to augment the data from the selected raw data.

The pre-processing step involves converting the raw data retrieved at S305 into a standard format that can be analysed. Since the data retrieved at S305 may be retrieved from multiple sources, this retrieved raw data may exist in multiple different formats. By pre-processing the data at S310, the information from the data is converted to a standard format for analysis. The pre-processing carried out at S310 also includes any necessary data cleansing operations. These operations are performed on the raw data to correct or remove any corrupt or inaccurate parts of the data.

At S315a, features and labels are extracted from the pre-processed data resulting from S310. The feature extraction comprises extracting information that is suitable for providing to a machine learning model from the data. This stage involves deriving from the data in the standard format, a set of input values (i.e. scores) representing the features for providing to a machine learning model. These features and labels are used for training one or more models during the training phase. The labels represent expected outputs from a model. Together the feature scores and labels constitute one or more training data sets.

At S320, the features and labels extracted from the data are used to train a model selected from amongst a plurality of candidate models. A candidate model is selected from a set of candidate models that is suitable for performing a particular analysis. For example, a first type of model may be suitable for determining the probability of different outcomes for diabetic patients. Another type of model may be more suitable for determining the probability of different outcomes for cancer patients. The selected model is trained in a supervised manner using the features and labels extracted at S315a. The model selection is made prior to the feature extraction process, with the features extracted from the data items being dependent upon the selected model.

During training at S320, the parameters (e.g. the weights for a neural network) of the model are tuned so as to reproduce the labels from the features. By doing so, a trained model is produced.

At S315b, feature extraction is performed for an operating phase. Input values representing features are determined from a set of data items (as discussed above for steps S305, S310, and S315a) and provided to a trained model during an operating phase. The operating data set that is determined at this step does not include the labels present in the training data set. Furthermore, each operating data set is associated with different patient.

At S325, the trained model is applied to the features extracted from a data set provided at S315b. The trained model outputs results, e.g. diagnoses or predictions as to negative patient outcomes, which at S330 can be analysed in a number of ways. The results may be displayed to a user on a user interface. The results may be used to inform decision making, e.g. by providing a recommended treatment for a patient. The results may be used to perform further analytics.

Further steps relating to the re-training and optimisation of the machine learning process are shown at S335 and S340 in FIG. 19. It would be appreciated that although these steps are shown along with the other steps as part of the machine learning process 300, in embodiments, they may not be performed in real time or continuously with the operation of the model at S325. Rather they may be performed separately from the operating process for obtaining results from the machine learning models.

At S335, the analysis of the outputs from at least one model is used to perform re-training of the at least one model. The re-training may be performed in dependence upon data provided at a later date that can be used to optimise the model. The newly available data can be used to produce new feature scores in the training data set.

One way in which the need for retraining may be highlighted may arise from changes in the threshold of the output from the machine learning model that yields certain predictions. Following the initial training of a model, during the operating phase an output of a certain value from the model may indicate a certain probability of a certain negative health outcome for the patient. For example, following the initial training, if a machine learning model for determining the risk of ovarian cancer outputs a value of 0.6, this may indicate that the patient has a probability of 50% of being referred for a consultation regarding ovarian cancer. However, as new types of data become available (e.g. a new type of scanning data), the threshold at which the output of the model corresponds to the patient having a 50% probability of being referred for a consultation regarding ovarian cancer rises (e.g. to 0.8) since the scanning data, which was not included as a model input parameter, now provides additional information not taken account of by a model, such that the output of the model carries less weight. Therefore, when the predictive value of the output of the model at a certain value shifts by a certain amount, it may be determined to perform retraining.

The retraining is performed by adding the newly available data to the set of data items and then recalculating the scores for the training data set as described. The new training data set may comprise one or more new feature scores, which could represent a new type of scanning data as discussed for the ovarian cancer model above. Using the new training data set comprising the new feature score, the relevant machine learning model is updated and retrained. In the case that the machine learning is a neural network, for example, the machine learning model is updated by adding an additional input node to the neural network. The additional input node receives the new feature score during the training phase for training the model. When the model has been trained, the model will receive an operating data set containing the new feature score which is input to the additional input node.

As an example, a model may applied to patient data to detect ovarian cancer. At a later point in time, it is discovered that a new health data variable may be useful in prediction of ovarian cancer. Therefore, the model is expanded to allow for an additional input variable (i.e. a feature score associated with the new health data variable). A new training data set is produced, including, for each a patient, the new feature score. The remaining feature scores of the new training data set may be generated in the same way as for the old training data set. The new training data set is then used to train the machine learning model. The new health data variable is then included in the subsequent operating data sets used to obtain results from the new model during the operating phase.

At S340, optimisation of one or more of the stages in the machine learning pipeline is carried out. This optimisation is carried out on the basis of the results and the analysis carried out at S330. For example, indications of the accuracy of the machine learning that are determined by comparing the results of the machine learning to future test results can be used to optimise different stages in the pipeline. The optimisation may involve comparing results from different models and selecting a model from amongst the candidate models in response to determining that this selected model yields superior results to another candidate model.

The optimisation involves optimising any of the other stages in the pipeline, such as modifying the data selection at S305 so as to modify the data selected from the databases 302 for analysis by one or more machine learning models. The optimisation may involve modifying the enrichment stage of the pipeline so that new or different types of data are used for augmenting data sets. The optimisation may involve modifying the format into which raw data is placed during pre-processing. The optimisation may involve modifying the feature extraction performed at S315a/S315b, so that different features are extracted or that different input values are used to represent the features.

Figure 20:
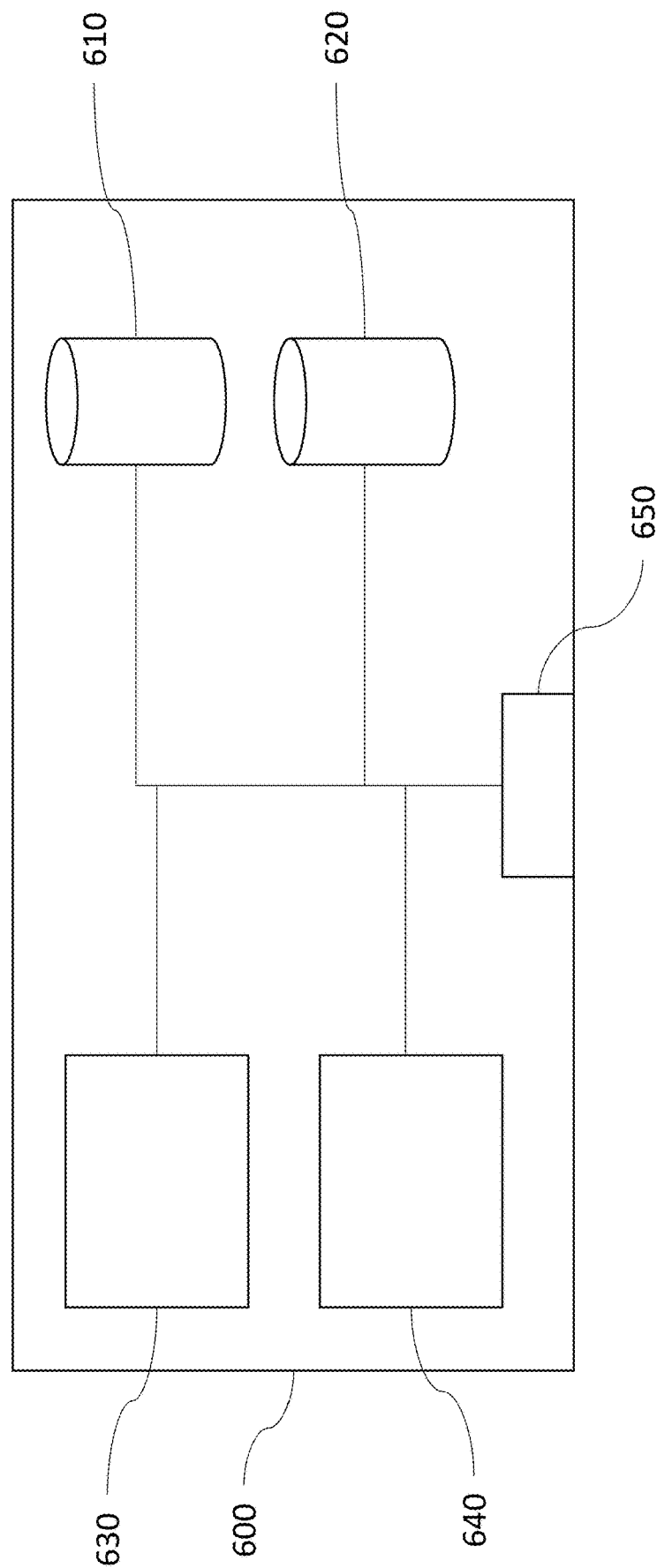
FIG. 20 is a schematic view of a system for implementing a process for training and operating machine learning models.

Reference is made to FIG. 20, which illustrates a data processing system 600, which may be used to train and/or run one or more machine learning models. The operating of trained one or more models and the training of the one or more models may be carried out on different systems (both exemplified by system 600) or on the same system 600. The system 600 may also run the conversion module used to produce the feature scores for training and operating the models. The system 600 is shown as a single enclosed apparatus. However, in some embodiments, the system 600 is a distributed system, with multiple data processing apparatuses operating in communication with one other. The system 600 may comprise a server, back-end system, or the like for performing processing on behalf of one or more client devices.

The system 600 comprises at least one random access memory 610, at least one read only memory 620, at least one data processing unit 620, 330 and an input/output interface 640. The memories 610, 620, store data for inputting to the one or more models and for storing results of the processing performing during execution of the one or more models. At least one of the memories 610, 620 store the data items associated with the patients and the training and operating data sets that are obtained from the data items by the conversion module. At least one of the memories 610, 620 additionally store computer executable code, which when executed provide the one or more machine learning models and the conversion module. At least one of the data processing units 630, 640 perform the processing associated with the one or more models, the training of the models, and any necessary pre-processing of data for use by the models. At least one of the data processing units 630, 640 execute the computer executable code to provide the one or more models and the conversion module. Via the interface 640, the system 600 receives the data items for constructing the training data sets and the data items for constructing the operating data sets. The system 600 additionally sends via the interface 650, the results produced by running the models on input data.

Figure 21:
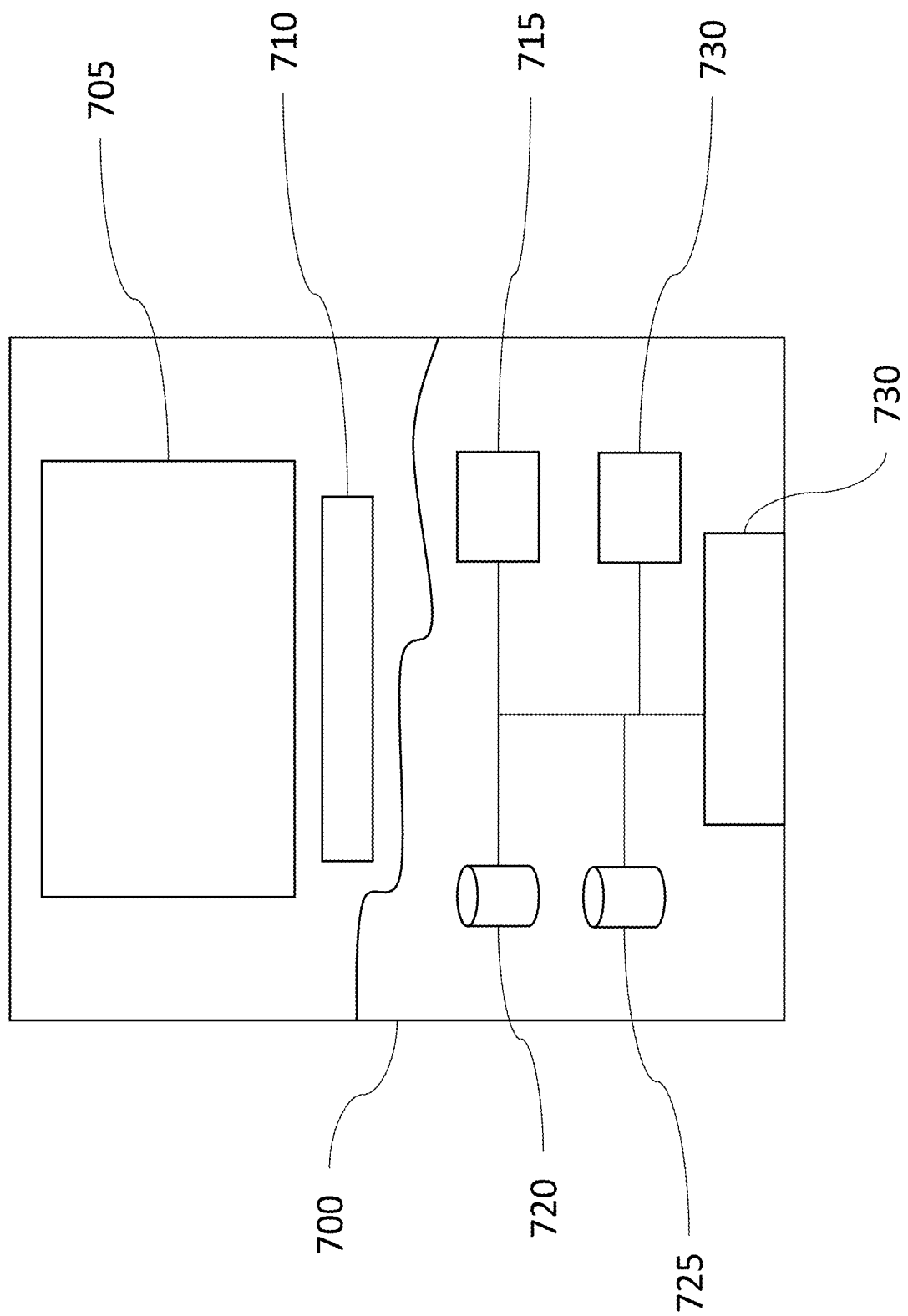
FIG. 21 is a schematic view of a user device for interacting with the system.

As noted, the system 600 on which data is processed using the one or more models may perform the processing on behalf of one or more client devices that are configured to communicate with the system 600. Reference is made to FIG. 21, which illustrates an example of an electronic device 700, which functions as such a client device. The electronic device 700 may be a mobile user equipment (UE), a personal computer (PC), a terminal or workstation or some other form of device.

The device 700 comprises an interface 730 over which it sends and receive signals with the system 700. The interface 730 may be a transceiver apparatus configured to send and receive communications over a radio interface. The transceiver apparatus may be provided, for example, by means of a radio part and associated antenna arrangement. The antenna arrangement may be arranged internally or externally to the device 700.

The device 700 is provided with at least one data processing entity 715, at least one random access memory 720, at least one read only memory 725, and other possible components 730 for use in software and hardware aided execution of tasks it is designed to perform, including control of, access to, and communications with access systems and other communication devices. The at least one random access memory 720 and the at least one read only memory 725 may be in communication with the data processing entity 715, which may be a data processor. The data processing, storage and other relevant control apparatus can be provided on an appropriate circuit board and/or in chipsets. A user may control the operation of the device 700 by means of a suitable user interface such as key pad 710, voice commands, touch sensitive screen or pad, combinations thereof or the like. A display 705, a speaker and a microphone can be also provided in the device 700. The display 705 enables a user to select data for processing by the system 600 and/or view results of the processing. Furthermore, the device 700 may comprise appropriate connectors (either wired or wireless) to other devices and/or for connecting external accessories, for example hands-free equipment, thereto.

At least one of the memories 720, 725 may be configured to store the data items that are used by the system 600 to construct the operating and/or training data sets. The at least one data processing entity 715 is configured to cause these data items to be sent via interface 730 to the system 600 for processing. The at least one data processing entity 715 may additionally or alternatively cause the sending of an instruction via interface 730 to cause data items to be retrieved from a further entity 600 and delivered to the system for constructing operating and/or training data sets.

The device 700 may additionally receive results (e.g. indications of negative health outcomes) of processing by one or more machine learning models operating on the system 600. These results are received by the interface 730 and stored in at least one of the memories 720, 725. The results may be displayed to a user of the device 700 on the display 705.

The invention claimed is:

1. A computer system for generating a quantitative value relating to a negative health outcome for a patient, the computer system comprising:
   a conversion module configured to receive multiple patient sets of data items, each patient set associated with a respective patient and each data item comprising a descriptor and the time at which that descriptor applied, the conversion module configured to generate multiple training data structures which each comprise, for each of the multiple patients, an array of selected features generated from the patient set of data items associated with that patient, the conversion module configured to generate for each selected feature a numerical value representing a score indicative of the relevance of that feature to the prediction of the negative health outcome for that patient, and a label indicating if that patient exhibits the negative health outcome, each training data structure having a different label corresponding to a different respective negative health outcome; and
multiple machine learning models, each of which is trained on a respective training data structure so as to be operable to generate a quantitative value relating to a respective negative health outcome for a patient with at least some of the features but for which the status of the negative health outcome is unknown, wherein at least some of the machine learning models which are trained relating to a different respective negative health outcome are trained using a training data structure with different sets of selected features with the different sets comprising at least some common features, wherein the conversion module is configured to generate the score for a particular one of the features for a particular one of the patients which varies between different training data sets for training different models.

2. A computer system according to claim 1, wherein at least some of the machine learning models which are trained with a label indicating a respective different negative health outcome are trained with a training data structure having a common set of selected features.

3. A computer system according to claim 1, wherein the conversion model is configured to receive additional data items in a patient's set and to modify the score(s) indicating the relevance of each feature affected by the additional data items for that patient set and generate a new training data structure including the modified score or scores for that patient.

4. A computer system according to claim 1, wherein the conversion module is configured to generate the score using a time related manipulation of numerical values associated with the descriptors of the data items.

5. A computer system according to claim 4, wherein the time related manipulation comprises a decay model wherein the score associated with a particular selected feature is reduced with time if that feature is not represented in subsequently received data items.

6. A computer system according to claim 1, wherein the conversion module is configured to generate the score associated with a particular feature in dependence upon the number of data items comprising a relevant descriptor for that feature, wherein the conversion module is configured to, when determining the score associated with the particular feature, evaluate a plurality of data items occurring within a time window as a single data item for purposes of determining the score associated with the particular feature.

7. A computer system according to claim 1, wherein the conversion model is configured to receive an additional data item in a patient's set and to generate a new training data structure including a new feature described by the additional data item for that patient set, wherein the computer system comprises a further machine learning model trained using the new training data structure.

8. A computer system according to claim 1, wherein the conversion module is configured to receive the multiple patients' sets of data items in a raw format and to map the data items of the raw format to a standard format comprising a pre-determined indicator code for each feature to form part of the descriptor.

9. A computer system according to claim 1, wherein the features are selected from:
symptoms;
test or procedures carried out on the patient;
test results for the patient;
personal data for the patient, the personal data comprising sensor data derived from at least one sensor configured to determine physiological information about the patient;
contextual data for the patient, the contextual data comprising physical environmental data; and/or
family history.

10. A computer system according to claim 9 comprising an interface for receiving the personal data, the personal data including sensor data derived from at least one sensor configured to determine physiological information about the patient, age of the patient, weight of the patient, genomic information of the patient, ethnicity of the patient, blood type of the patient, etc.

11. A computer system according to claim 10 configured to receive the sensor data from at least one wearable device worn by the patient.

12. A computer system according to claim 11 configured to derive the contextual data from an external data source, the contextual data comprising location data, physical environmental data (e.g. weather), social environmental data (e.g. deprivation index), or social data for a patient (e.g. the marital status of the patient).

13. A computer system according to claim 1, wherein the negative health outcome is a disease or a disease complication.

14. A computer system according to claim 1, wherein the negative health outcome comprises a disease in the groups: cardiovascular diseases, cancers, respiratory diseases, and diabetes.

15. A computer system according to claim 1, wherein the negative health outcome is a disease complication comprising at least one of nephropathy; neuropathy; retinopathy; diabetic foot; and atrial fibrillation.

16. A computer system according to claim 1, wherein the conversion module comprises at least one computer on which is executed a computer program configured to generate the multiple training data structures from the received multiple patient sets of data items, and an interface for receiving the multiple patient sets of data items and connected to supply them to the at least one computer.

17. A computer implemented method for training a machine learning model so as to be operable to generate a quantitative value relating to a negative health outcome for a patient, the method comprising:
generating multiple training data structures, each from multiple patient sets of data items, each patient set associated with a patient and each data item comprising a descriptor of a health impacting event and the time at which that event impacted the patient, wherein each training data structure comprises, for each patient, an array of selected features, each selected feature associated with a numerical value representing a score indicative of the relevance of that feature to the prediction of the negative health outcome, and a label indicating if the patient exhibits the negative health outcome, each training data structure having a different label corresponding to a different respective negative health outcome; and
applying the multiple training data structures to respective machine learning models to thereby train the machine learning models,
wherein:
each training data structure has a different label relating to a different negative health outcome; and at least some of the machine learning models which are trained relating to a different respective negative health outcome are trained using a training data structure with different sets of selected features with the different sets comprising at least some common features;

the method comprising applying one or more of the trained models to features extracted from a patient data set, each trained model outputting results, comprising diagnoses or predictions as to a particular negative health outcome;

the method further comprising suppressing the output of one of the machine learning models for a predefined time period when it is determined, independently of the model output, that the probability of the particular negative health outcome in the result of that model is below a threshold value.

18. A method according to claim 17, comprising generating the score using a time related manipulation of numerical values associated with the descriptors of the data items.

19. A method according to claim 17, wherein the suppressing comprises setting the output to zero.

20. A method according to claim 17, wherein the method comprises interrupting the suppressing to deliver the output in response to a further diagnostic event which increases the probability of the patient exhibiting the particular negative health outcome.

* * * * *